(12) United States Patent
Banoglu et al.

(10) Patent No.: US 11,622,966 B2
(45) Date of Patent: Apr. 11, 2023

(54) HIGHLY POTENT TACC3 INHIBITOR AS A NOVEL ANTICANCER DRUG CANDIDATE

(71) Applicants: A2A Pharmaceuticals, Inc., New York, NY (US); OncoCube Therapeutics LLC, Wilmington, DE (US)

(72) Inventors: Erden Banoglu, Ankara (TR); Burcu Caliskan, Ankara (TR); Ozgur Sahin, Lexington, SC (US); Deniz Lengerli, Ankara (TR); Ozge Akbulut, Ankara (TR)

(73) Assignees: A2A Pharmaceuticals, Inc., New York, NY (US); OncoCube Therapeutics LLC, Wilmington, DE (US)

( * ) Notice: Subject to any disclaimer, the term of this patent is extended or adjusted under 35 U.S.C. 154(b) by 188 days.

(21) Appl. No.: 17/058,982

(22) PCT Filed: Mar. 14, 2019

(86) PCT No.: PCT/TR2019/050164
§ 371 (c)(1),
(2) Date: Nov. 25, 2020

(87) PCT Pub. No.: WO2020/018039
PCT Pub. Date: Jan. 23, 2020

(65) Prior Publication Data
US 2021/0220369 A1  Jul. 22, 2021

(30) Foreign Application Priority Data
May 25, 2018 (TR) .................. 2018/07464

(51) Int. Cl.
*A61K 31/5377* (2006.01)
*A61P 35/00* (2006.01)

(52) U.S. Cl.
CPC .......... *A61K 31/5377* (2013.01); *A61P 35/00* (2018.01)

(58) Field of Classification Search
CPC ...... A61K 31/00; A61K 31/33; A61K 31/395; A61K 31/535; A61K 31/5375; A61K 31/5377; A61P 35/00
See application file for complete search history.

(56) References Cited

U.S. PATENT DOCUMENTS

| | | | |
|---|---|---|---|
| 9,630,953 B2 * | 4/2017 | Yao | .................... A61K 31/4465 |
| 2016/0332989 A1 | 11/2016 | Wu et al. | |
| 2019/0337926 A1 | 11/2019 | Hashizume et al. | |

FOREIGN PATENT DOCUMENTS

| CN | 107089968 A | 8/2017 |
|---|---|---|
| EP | 2857392 A1 | 4/2015 |
| JP | 2016/065869 A | 4/2016 |
| WO | WO-03/018022 A1 | 3/2003 |
| WO | WO-2007/026251 A2 | 3/2007 |
| WO | WO-2008/005538 A2 | 1/2008 |
| WO | WO-2011/120026 A1 | 9/2011 |
| WO | WO-2015/082583 A1 | 6/2015 |
| WO | WO-2016/146220 A1 | 9/2016 |
| WO | WO-2016/173557 A1 | 11/2016 |
| WO | WO-2016/196776 A2 | 12/2016 |
| WO | WO-2017/136315 A1 | 8/2017 |
| WO | WO-2018/002217 A1 | 1/2018 |
| WO | WO-2018/045957 A1 | 3/2018 |
| WO | WO-2018/231910 A1 | 12/2018 |
| WO | WO-2019/101843 A1 | 5/2019 |
| WO | WO-2019/161224 A1 | 8/2019 |
| WO | WO-2019/177374 A1 | 9/2019 |
| WO | WO-2020/018039 A2 | 1/2020 |
| WO | WO-2021/030623 A1 | 2/2021 |

OTHER PUBLICATIONS

Ha, GH., Kim, JL., Petersson, A. et al. TACC3 deregulates the DNA damage response and confers sensitivity to radiation and PARP inhibition. Oncogene 34, 1667-1678 (2015). (Year: 2015).*
Geun-Hyoung Ha, Jung-Lye Kim, Eun-Kyoung Yim Breuer. Transforming acidic coiled-coil proteins (TACCs) in human cancer, Cancer Letters, vol. 336, Issue 1, 2013, pp. 24-33. (Year: 2013).*
Loredana Campo, Eun-Kyoung Breuer. Inhibition of TACC3 by a small molecule inhibitor in breast cancer, Biochemical and Biophysical Research Communications, vol. 498, Issue 4, 2018, pp. 1085-1092. (Year: 2018).*
Extended European Search Report for EP Application No. EP 19837587 dated Mar. 9, 2022.
Campo et al., "Inhibition of TACC3 by a small molecule inhibitor in breast cancer," Biochemical and Biophysical Research Communications, 498(4): 1085-1092 (2018).
Extended European Search Report for EP Application No. 19209120.5 dated Mar. 17, 2020.
International Search Report and Written Opinion for International Application No. PCT/TR2019/050164 dated Feb. 21, 2020.
International Search Report and Written Opinion for International Application No. PCT/TR2019/050951 dated Aug. 14, 2020.
Wurdak et al., "A small molecule accelerates neuronal differentiation in the adult rat," PNAS, 107(38): 16542-16547 (2010).
Yao et al. "A small compound targeting TACC3 revealed its different spatiotemporal contributions for spindle assembly in cancer cells," Oncogene, 33(33): 4242-4252 (2013).
Akbulut et al., "A Highly Potent TACC3 Inhibitor as a Novel Anticancer Drug Candidate," Molecular Cancer Therapeutics, 19(6): 1243-1254 (2020).

(Continued)

*Primary Examiner* — Brandon J Fetterolf
*Assistant Examiner* — Manahil Mirghani Ali Abdalhameed
(74) *Attorney, Agent, or Firm* — Foley Hoag LLP; Lucas P. Watkins; Alexander J. Chatterley

(57) ABSTRACT

The present invention relates to a new inhibitor chemotype 3-(4-methoxyphenyl)-N-(2-morpholinopyrimidin-4-yl) isoxazol-5-amine (BO-264) targeting TACC3 protein with high potency as a mitotic blocker for the treatment of breast and potentially other cancers.

18 Claims, 17 Drawing Sheets

(56) References Cited

OTHER PUBLICATIONS

Figure 1:
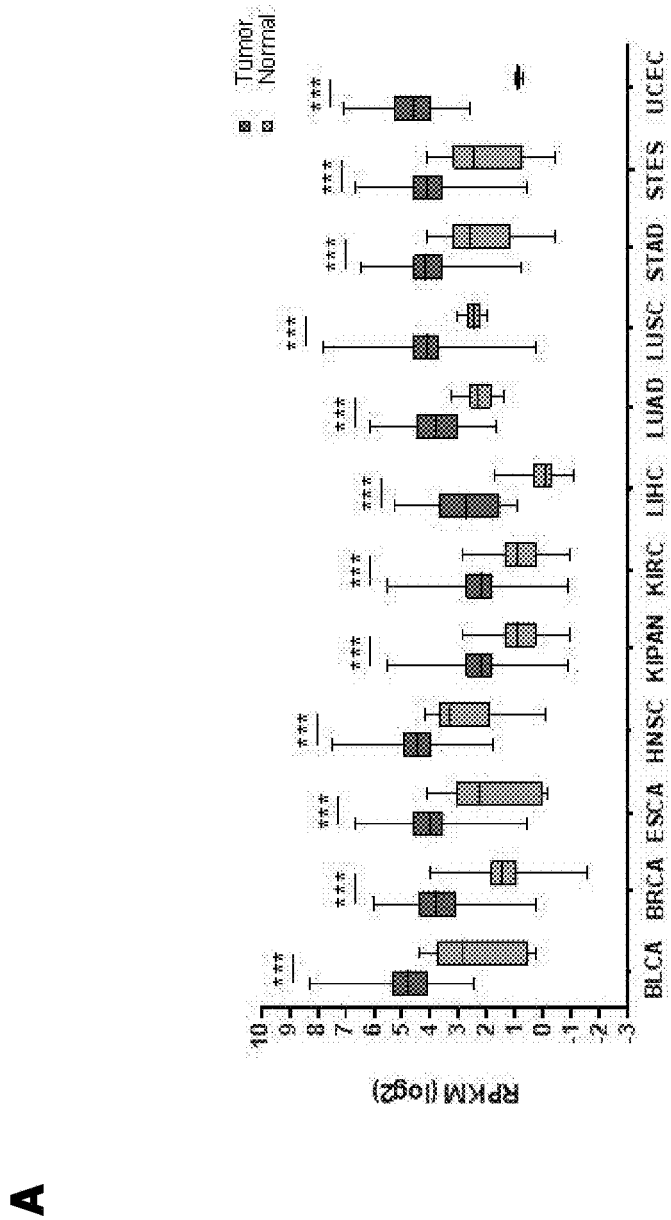
Figure 1:
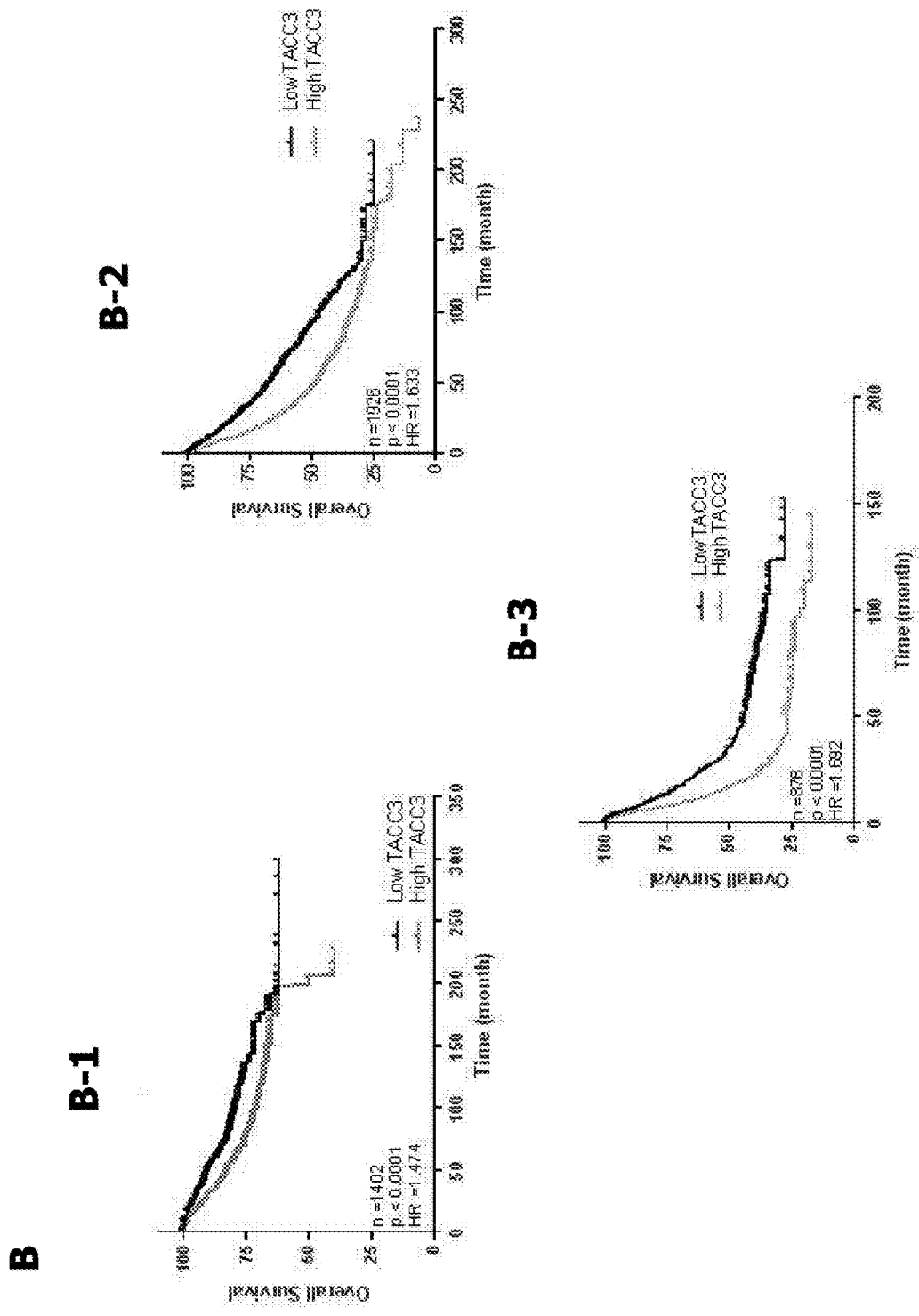

Akbulut et al., "A novel TACC3 inhibitor as an anti-cancer agent in breast cancer [abstract]," Cancer Research, 79(13): 4 pages (2019).
Akbulut et al., "A novel TACC3 inhibitor as an anti-cancer agent in breast cancer [abstract]," European Journal of Cancer, 103(S1): e71 Abstract 200(PB-051)(2018).
CAS Registry No. 2322029-91-2; CA Index Name: 4-Pyrimidinamine, 6-ethyl-5-fluoro-N-[3-(2-thienyl)-5-isoxazolyl]-; Entered STN: May 31, 2019.
CAS Registry No. 2326659-25-8; CA Index Name: 4-Pyrimidinamine, N-[3-(2-thienyl)-5-isoxazolyl]-6-(trifluoromethyl)-; Entered STN: Jun. 9, 2019.
CAS Registry No. 2328417-44-1; CA Index Name: 4-Pyrimidinamine, 2-cyclopropyl-6-methyl-N-[3-(2-thienyl)-5-isoxazolyl]-; Entered STN: Jun. 11, 2019.
CAS Registry No. 2329636-00-0; CA Index Name: 4-Pyrimidinamine, 6-ethyl-N-[3-(2-thienyl)-5-isoxazolyl]-; Entered STN: Jun. 11, 2019.
CAS Registry No. 2329672-37-7; CA Index Name: 4-Pyrimidinamine, 2-methyl-N-[3-(2-thienyl)-5-isoxazolyl]-6-(trifluoromethyl)-; Entered STN: Jun. 11, 2019.
CAS Registry No. 2329697-20-1; CA Index Name: 2-Pyridinecarboxylic acid, 4-[[3-(2-thienyl)-5-isoxazolyl]amino]-, methyl ester; Entered STN: Jun. 11, 2019.
CAS Registry No. 2329701-76-8; CA Index Name: 4-Pyrimidinamine, 5,6-dimethyl-N-[3-(2-thienyl)-5-isoxazolyl]-; Entered STN: Jun. 11, 2019.
CAS Registry No. 2329961-45-5; CA Index Name: 4-Pyrimidinamine, 2-(1-methylethyl)-N-[3-(2-thienyl)-5-isoxazolyl]-; Entered STN: Jun. 12, 2019.
CAS Registry No. 2330400-57-0; CA Index Name: 4-Pyrimidinamine, 2-methyl-N-[3-(2-thienyl)-5-isoxazolyl]-; Entered STN: Jun. 12, 2019.
CAS Registry No. 2330488-91-8; CA Index Name: 4-Pyrimidinamine, 2,6-dimethyl-N-[3-(2-thienyl)-5-isoxazolyl]-; Entered STN: Jun. 12, 2019.
CAS Registry No. 2330625-68-6; CA Index Name: 4-Pyrimidinamine, 6-methyl-N-[3-(2-thienyl)-5-isoxazolyl]-; Entered STN: Jun. 12, 2019.
International Search Report and Written Opinion for International Application No. PCT/US2020/060588 dated Mar. 4, 2021.
Lengerli et al., "Studies On the Synthesis and Anticancer Potential of Novel 2,4-Diaminopyrimidine Derivatives," EFMC-YMSC Abstract: 1 page (Sep. 8, 2022).
Lin et al., "Discovery and evaluation of 3-phenyl-1 H-5-pyrazolylamine-based derivatives as potent, selective and efficacious inhibitors of FMS-like tyrosine kinase-3 (FLT3). Bioorganic & medicinal chemistry", 19(14): 4173-4182, (2011).
Turk et al., "From cancer to pain target by automated selectivity inversion of a clinical candidate", Journal of Medicinal Chemistry, 61(11): 4851-4859, (2018).
Turkish Examination Report for TR application No. 2018/07464 dated Jun. 28, 2020.
Turkish Search Report for TR application No. 2018/07464 dated Feb. 21, 2020.

\* cited by examiner

Reagent and conditions: (a) SOCl$_2$, EtOH, reflux, 3h; (b) NaH, MeCN, toluene, reflux, 2h; (c) NH$_2$OH.HCl, NaOH, H$_2$O, reflux, 4h; (d) t-BuOK, 2,4-dichloropyrimidine, t-BuOH, rt, 24h; (e) Morpholine, n-butanol, reflux, 5h.

| Molecular Weight (g/mol) | 353.38 | | |
|---|---|---|---|
| Solubility at pH 7.4 (µM)[a] | < 1 | | |
| LogD at pH 7.4[b] | 2.31 | | |
| Human PPB (%bound)[c] | 98.87 | | |
| T$_{1/2}$ (min)[d] | 5$_{(MLM)}$ | | |
| | 12$_{(HLM)}$ | | |
| Cl$_{int}$ (µL/min/mg protein)[e] | 329.2$_{(MLM)}$ | | |
| | 117.5$_{(HLM)}$ | | |
| CYP (IC$_{50}$ µM)[f] | CYP2C9 | CYP2D6 | CYP3A4 |
| | 2.63 ± 0.19 | 18.46 ± 0.23 | 30.04 ± 4.24 |
| | | | CYP3A4 |
| | | | 8.59 ± 1.68 |
| Caco-2 P$_{app}$ (nm/s)[g] | 190.60 ± 61.82 (A→B) | | 241.03 ± 8.18 (B→A) |

[a]Kinetic solubility in sodium phosphate buffer at pH 7.4 at 25°C after 2 h (Buttar et al., 2010). [b]LogD: distrubution coefficient in octanol/sodium phosphate buffer (50 mM, pH 7.4) (Unger et al., 1978). [c]PPB: plasma protein binding assessed by equilibrium dialysis in human at 37°C (Buttar et al., 2010). [d]T$_{1/2}$: half life in mouse and human liver microsomes (MLM and HLM respectively) (Kalvass et al., 2001). [e]Cl$_{int}$: intrinsic clearance in MLM and HLM (Kalvass et al., 2001). [f]CYP: cytochrome P450 isozymes inhibition by BO-264 evaluated in HLM (Bourrie et al., 1996). [g]P$_{app}$: apperant permeability coefficients in Caco-2 cell monolayer (Camenisch et al., 1998).

Figure 12

HIGHLY POTENT TACC3 INHIBITOR AS A NOVEL ANTICANCER DRUG CANDIDATE

RELATED APPLICATIONS

This application is a § 371 national-stage application based on PCT Application No. PCT/TR2019/050164, filed Mar. 14, 2019, which claims priority to Turkish Application No. 2018/07464, filed May 25, 2018, now Turkish Patent No. 201807464. The contents of PCT/TR2019/050164 are hereby incorporated by reference in its entirety.

TECHNICAL FIELD

The present invention relates to a new inhibitor chemotype 3-(4-methoxyphenyl)-N-(2-morpholinopyrimidin-4-yl) isoxazol-5-amine (BO-264) targeting transforming acidic coiled-coil protein 3 (TACC3). The present invention also relates to anti-cancer agent role of TACC3 inhibitor molecule: BO-264.

BACKGROUND OF THE INVENTION (PRIOR ART)

Cancer is a complex disease characterized by uncontrolled cell division. Among cancer types, breast cancer is the most common cancer among women and is one of the main reasons of cancer deaths. With the understanding of tumor biology, targeted medical therapies have continuously been developed to increase the patient survival rate.

Although the Food and Drug Administration (FDA) has approved approximately two dozen drugs to be used for the treatment of breast cancer, there are still half a million breast cancer death all round the world each year. In particular, considering the side effects of currently available chemotherapy agents, development of targeted therapies causing less toxicity have been a major focus in recent years. Since cancer is characterized as abnormal and uncontrollable cell growth with the potential to invade or spread to the other parts of the body or a malignant tumor, drugs or substances that target and inhibit the function of specific macromolecules responsible for the proliferation and survival of tumor cells are used in breast cancer-targeted therapies.

Since microtubule re-organization is an important step during cell division, drugs that interfere with this process have been a major focus of cancer research. Antimitotic drugs disrupt the polymerization dynamics of microtubules by activating the spindle assembly check point (SAC), which prevents the transition from metaphase to anaphase. As a result, cells stop division, and these mitotically arrested cells eventually die. A continuous investigation of the mechanism of mitotic events may lead to new target protein candidates and/or pathways, which is very important for providing more effective therapeutic options for cancer patients. Anti-microtubule agents, such as *vinca* alkaloids, maytansinoids and taxanes are examples of such drugs that are widely used as chemotherapeutic agents for a variety of tumors (Marzo & Naval, 2013). However, a significant concern about these drugs is the drug toxicity to non-tumorigenic cells resulting in serious side effects.

Drug resistance is also another major problem leaving patient's response to these drugs highly unpredictable (Gascoigne & Taylor, 2009). To overcome these problems and improve chemotherapy response, anti-mitotic, cancer specific therapies targeting mitosis-specific kinases and microtubule-motor proteins were identified (Dominguez-Brauer et al., 2015). Importantly, as phosphorylation is a critical step in cell cycle regulation and spindle assembly, kinases having role in these processes have been studied for a long time as potential targets. Among these, specific inhibitors against cyclin-dependent kinases (CDKs), Aurora kinases and Polo-like kinases (PLKs) have been developed and clinically tested (Sanchez-Martinez, Gelbert, Lallena, & de Dios, 2015; Strebhardt & Ullrich, 2006; Tang et al., 2017). Compared to anti-microtubule agents, none of these anti-mitotic drugs demonstrated a spectacular clinical outcome despite their low toxicity profile, leading to limited clinical efficiency (Chan, Koh, & Li, 2012). Thus, alternative target molecules that selectively and effectively target dividing cancer cells remain to be elucidated and developed.

TACC3, one of the TACC members, is a non-kinase microtubule binding protein and plays a key role in centrosome regulation and ensures microtubule stability (Singh, Thomas, Gireesh, & Manna, 2014). This gene also has an important role in the nucleation of TACC3 centrosomal microtubules. Its elevated levels are observed in many cancer types including prostate cancer, hepatocellular carcinoma, non-small cell lung cancer and breast cancer. Accordingly, knockdown of TACC3 suppresses tumorigenesis and cell growth in renal cell carcinoma (RCC) (Guo & Liu, 2018). Disruption of TACC3 function also causes a range of different cellular outcomes including multi-polar spindle formation leading to mitotic arrest (Yao et al., 2012), chromosome misalignment resulting in caspase-dependent apoptosis (Schneider et al., 2007) and, in some cases, senescence (Schmidt et al., 2010). These studies show that TACC3 is a critical molecule enrolled in spindle assembly of cancer cells, which makes it an important potential target for cancer targeted therapy.

KHS101, a small molecule TACC3 inhibitor, was first identified to promote neuronal differentiation in rats (Wurdak et al., 2010). Although tumor growth of glioblastoma (GBM) xenografts were suppressed through KHS101 treatment (Polson et al., 2018), it requires to be pharmacologically optimized in order to be translated into clinics due to low systemic stability and high working doses (Wurdak et al., 2010). Another TACC3 inhibitor, SPL-B, has been shown to inhibit the centrosome microtubule nucleation in ovarian cancer cells and suppress tumor growth in ovarian cancer xenografts (Yao et al., 2014). In conclusion; currently available TACC3 inhibitors, KHS101 and SPL-B, were shown to reduce tumor growth in glioblastoma and ovarian cancer xenografts, respectively. However, none of these inhibitors has yet reached to clinical phases due to high IC50 (50% inhibitory concentration) or low systemic stability, which encourages developing a novel potent TACC3 inhibitor having potential to be translated into clinics.

Within the frame of a recent screening approach for novel chemotypes that antagonize TACC3 function in in vitro and in vivo systems, which can be used as a general mitotic blocker in cancer treatment, compound 5 (3-(4-methoxyphenyl)-N-(2-morpholinopyrimidin-4-yl)isoxazol-5-amine, BO-264) was identified. BO-264 significantly inhibited the proliferation of JIMT-1 breast cancer cell lines (IC50=232 nM), which express high TACC3 protein level and shows tumorigenicity with well documented progression in both mouse models and several human cell culture systems (Saatci et al., 2018; Tanner et al., 2004).

BRIEF DESCRIPTION OF THE INVENTION

The main object of the present invention is to reduce undesirable side effects by using smaller doses of TACC3 inhibitor than specific inhibitors available in the cancer therapy.

The aim of the present invention is to provide a novel TACC3 inhibitor with high potency as a mitotic blocker for the treatment of breast and potentially other cancers by targeting the TACC3 protein.

Another object of the present invention is to provide a new chemotype BO-264 for use in treating cancer.

BO-264 showed a superior anti-proliferative effect to known TACC3 inhibitors in different breast cancer cell lines with different subtypes while it has minor effects on normal breast cell line. In addition to breast cancer cells, BO-264 demonstrated highly effective cytotoxicity (~90% have less than 1 µM GI50 value) against multiple cancer types including colon, melanoma, lung, central nervous system, ovarian, leukemia, renal and prostate cancer cell lines in the NCI-60 panel.

Furthermore, BO-264 was found to induce mitotic arrest, apoptosis and DNA damage at lower doses compared to other two TACC3 inhibitors. Significantly, oral administration of BO-264 suppressed tumor growth in breast cancer xenografts in immunodeficient mice. Therefore, the present invention is a novel TACC3 inhibitor with high potency as a mitotic blocker for the treatment of breast and potentially other cancers.

The present invention (i) provides a comprehensive analysis of BO-264 on breast cancer cell lines, (ii) reveals that this compound showed superior effects on various cellular processes, such as mitotic arrest, DNA damage and apoptosis to other available TACC3 inhibitors, and (iii) demonstrates anti-tumor effectiveness with no toxicity of BO-264 orally in breast cancer xenografts potentially suggesting that it can be used as a mitotic blocker for the treatment for breast cancer.

TACC3-BO-264 binding was validated through target engagement assay and isothermal titration calorimetry (ITC) methods.

FIGURES

FIG. 1: TACC3 is upregulated in various cancer types and its high-levels associate with worse overall survival in different cancer types. (A) Differential mRNA expression plots for TACC3 between tumor and normal tissues of TCGA patients represented as Reads Per Kilobase Million (RPKM) (log 2) values. ***: p<0.001. (BLCA: Bladder Urothelial Carcinoma; BRCA: Breast Invasive Carcinoma; ESCA: Esophageal Carcinoma; HNSC: Head and Neck Squamous Cell Carcinoma; KIPAN: Pan Kidney Cohort (KICH+KIRC+KIRP); KIRC: Kidney Renal Clear Cell Carcinoma; LIHC: Liver Hepatocellular Carcinoma; LUAD: Lung Adenocarcinoma; LUSC: Lung Squamus Cell Carcinoma; STAD: Stomach Adenocarcinoma; STES: Stomach and Esophageal Carcinoma; UCEC: Uterine Corpus Endometrial Carcinoma) (B) Effect of TACC3 level on overall survival of breast (B-1), lung (B-2) and gastric cancer (B-3) patients from KM Plotter database (Gyorffy, Lanczky et al. 2010; Gyorffy, Surowiak et al. 2013; Szasz, Lanczky et al. 2016).

Figure 2:
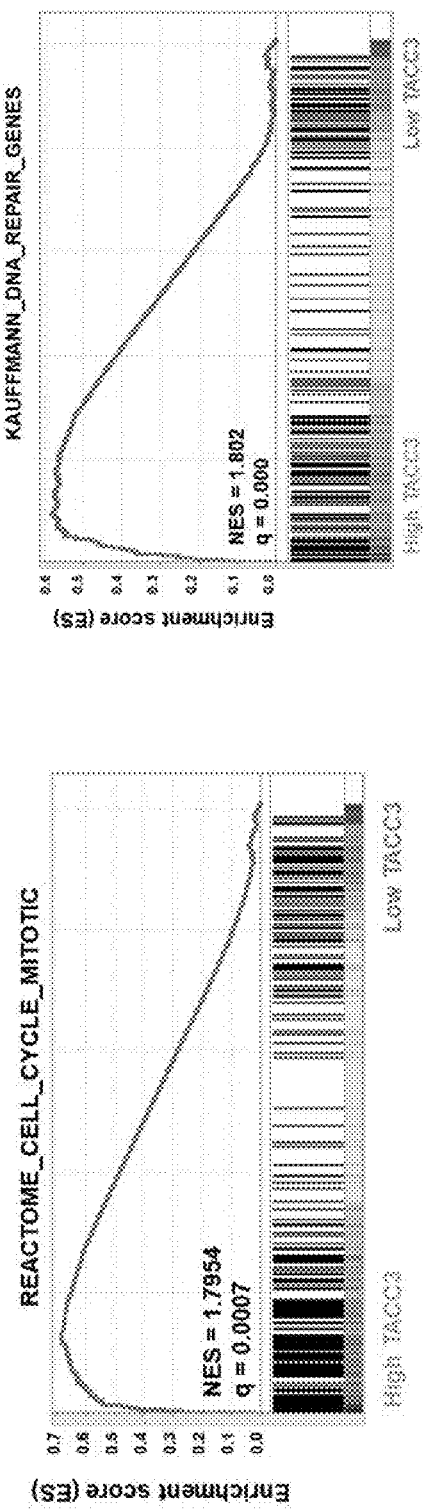
Figure 2:
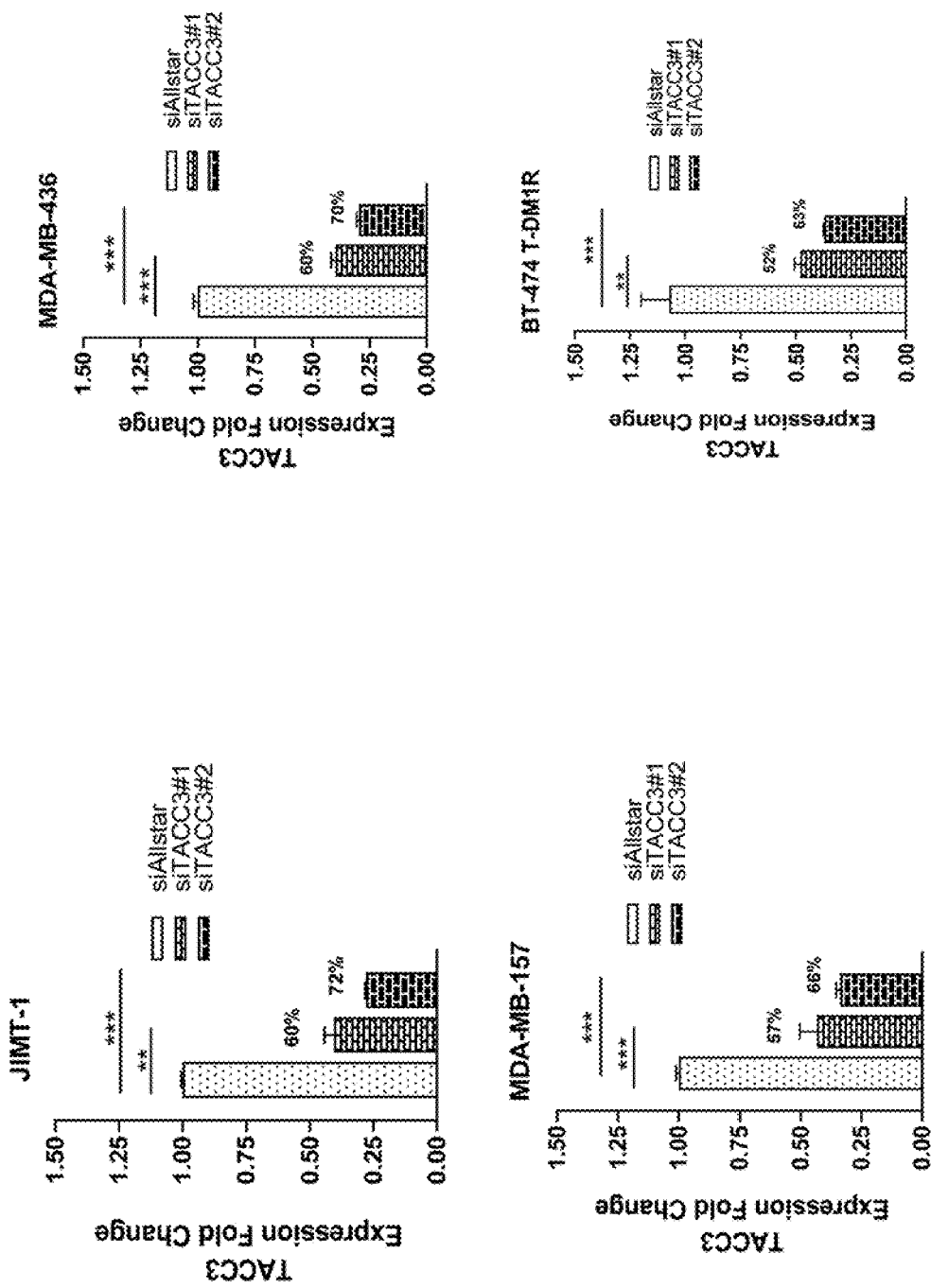
Figure 2:
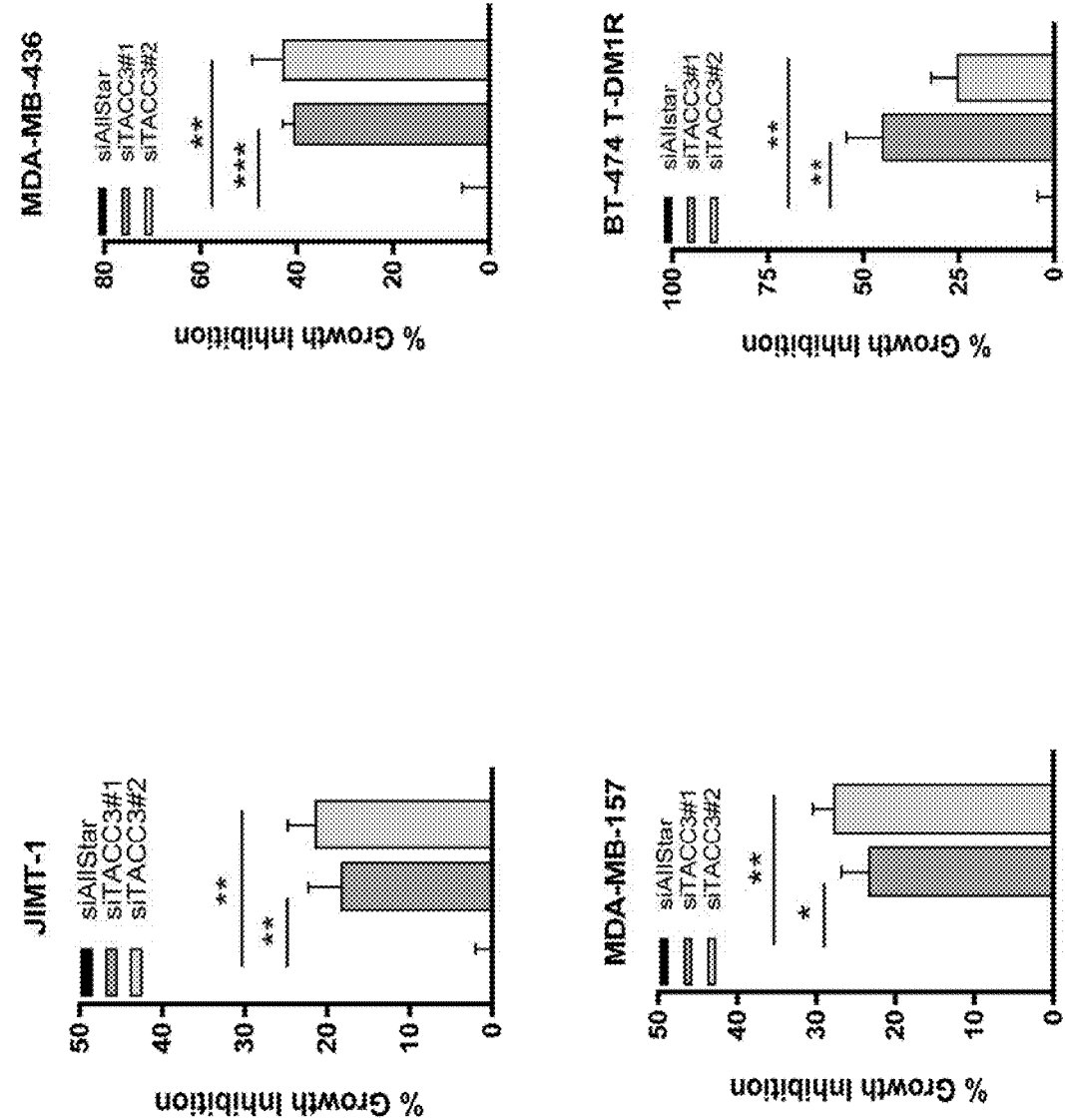
Figure 2:
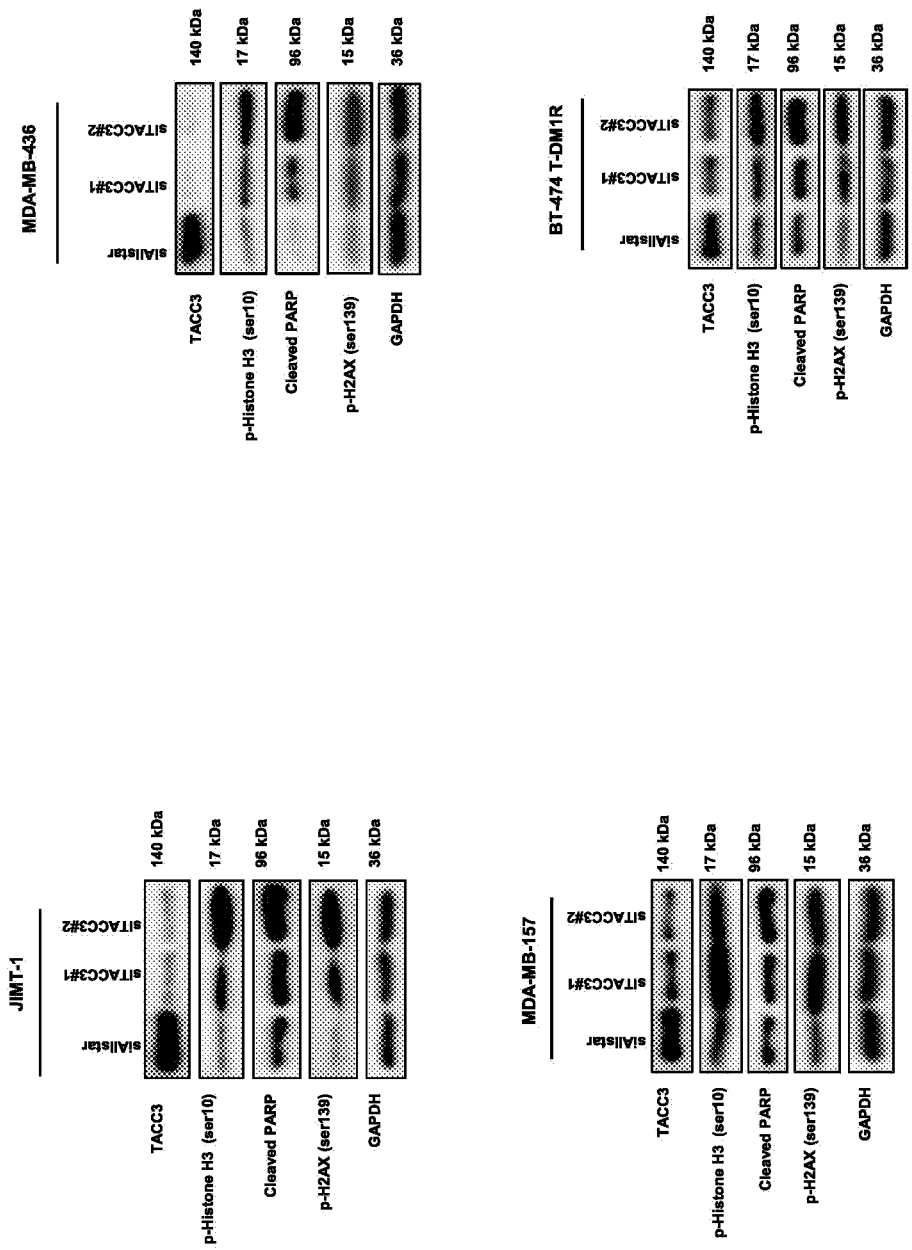

FIG. 2: Mitosis and DNA repair processes are enriched in patients with high TACC3 levels, and TACC3 inhibition induces mitotic arrest, DNA damage and apoptosis. (A) Gene set enrichment analysis (GSEA) of mitosis and DNA repair-related gene sets in breast cancer METABRIC Validation data set (n=995) (Curtis et al. 2012) with respect to their TACC3 expression level. Data significance is presented as Normalized Enrichment Score (NES) and FDR (q) value. (B) qRT-PCR showing knockdown efficiency of TACC3-specific siRNAs in breast cancer cell lines. Cells were transfected with 20 nM of two different siRNAs against TACC3, and TACC3 mRNA level was examined after 48 h of transfection. Percentages on the graphs show the knockdown efficiency. (C) Proliferation of breast cancer cells upon TACC3 knockdown with two different siRNAs. Cells were transfected with siRNAs targeting TACC3, and cell viability was measured after 72 h of transfection. (D) Western blot analysis of mitotic arrest, apoptosis and DNA damage markers in breast cancer cells upon TACC3 knockdown. GAPDH was used as a protein loading control. *: p <0.05; : p<0.01; *: p<0.001.

Figure 3:
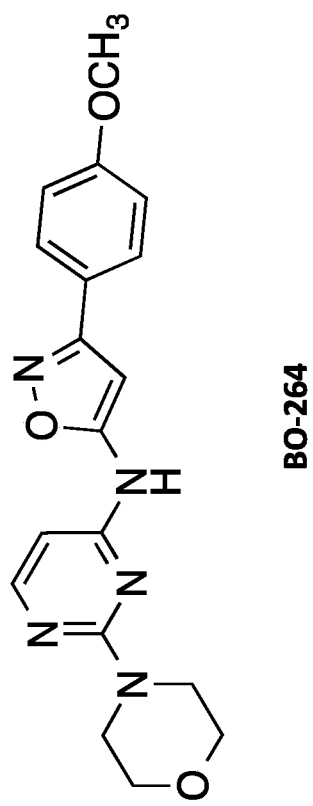

FIG. 3. Chemical structure of the novel inhibitor of TACC3: BO-264

Figure 4:
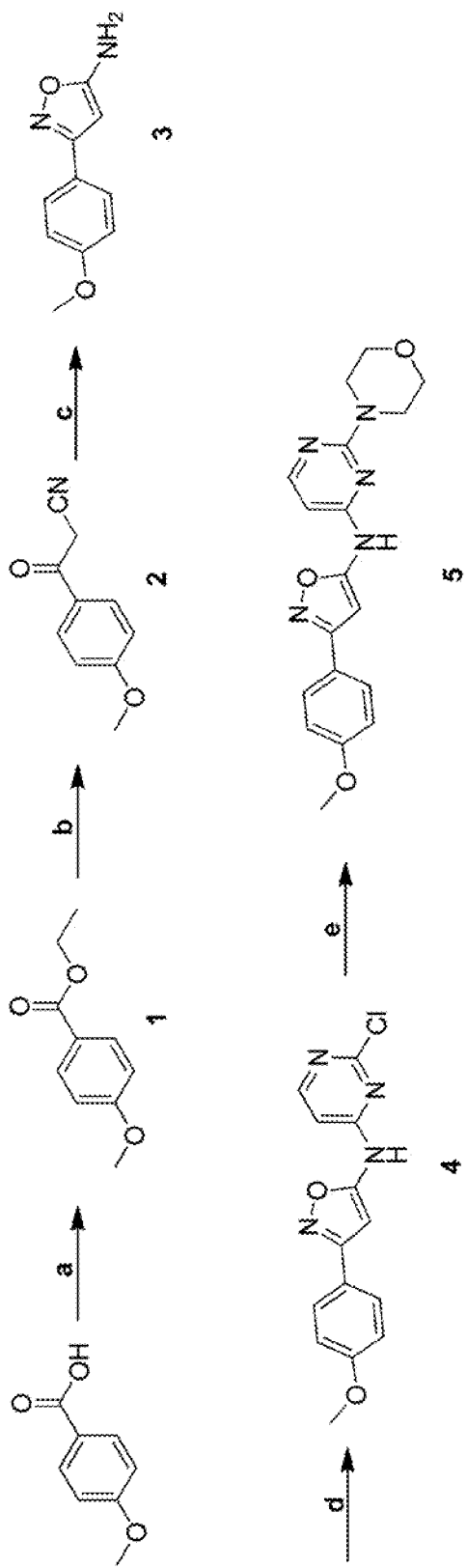

FIG. 4. Synthesis scheme of BO-264. Reagent and conditions: (a) $SOCl_2$, EtOH, reflux, 3 h; (b) NaH, MeCN, toluene, reflux, 2 h; (c) $H_2NOH.HCl$, NaOH, $H_2O$, reflux, 4 h; (d) t-BuOK, 2,4-dichloropyrimidine, t-BuOH, rt, 24 h; (e) Morpholine, n-butanol, reflux, 5 h.

Figure 5:
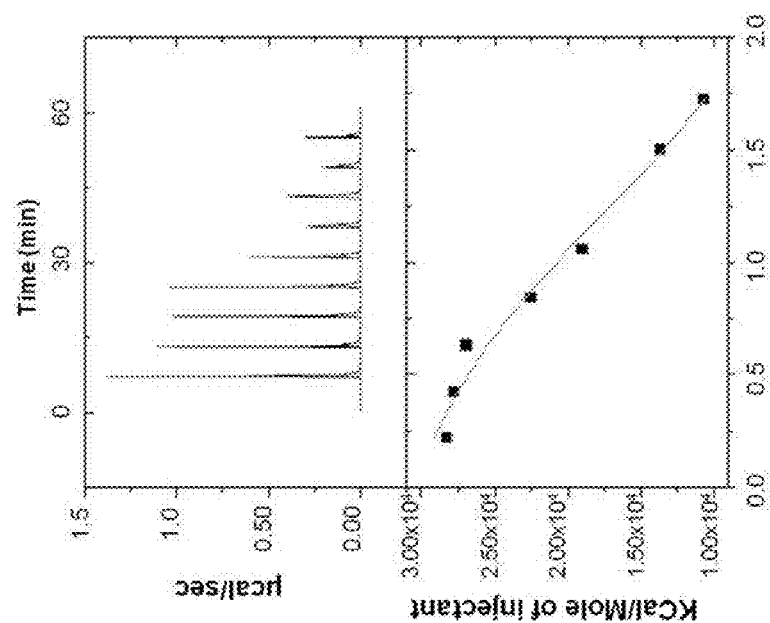

FIG. 5. BO-264 is a novel TACC3 inhibitor binding to TACC3. Determination of TACC3 and BO-264 interaction using isothermal titration calorimetry. Upper trace shows raw data while lower trace shows integrated data from a titration of TACC3 into BO-264 (10 fold higher concentration in the syringe). Model fitting of a single interaction model was applied using the Origin 7 software provided along with the ITC200 instrument.

Figure 6:
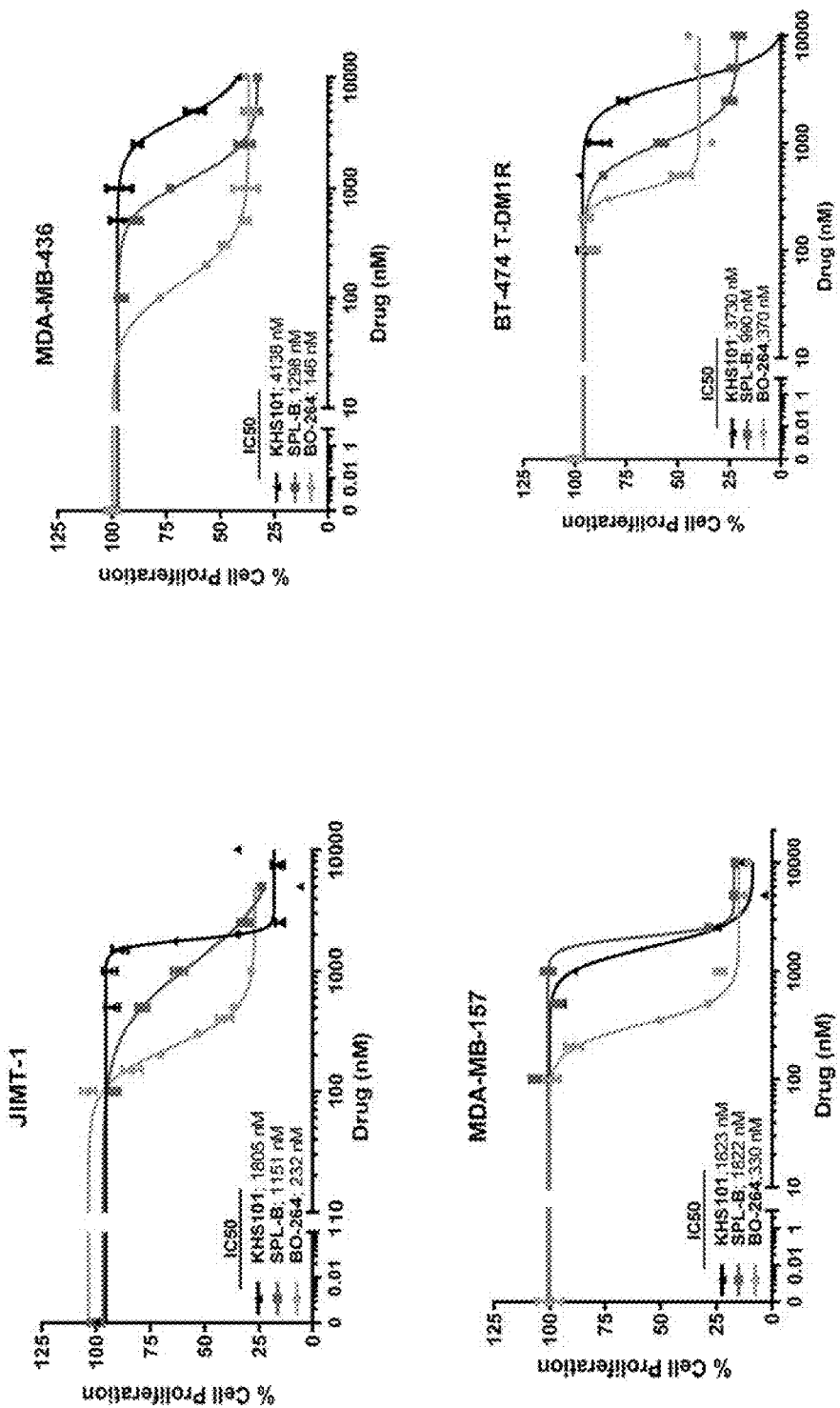
Figure 6:
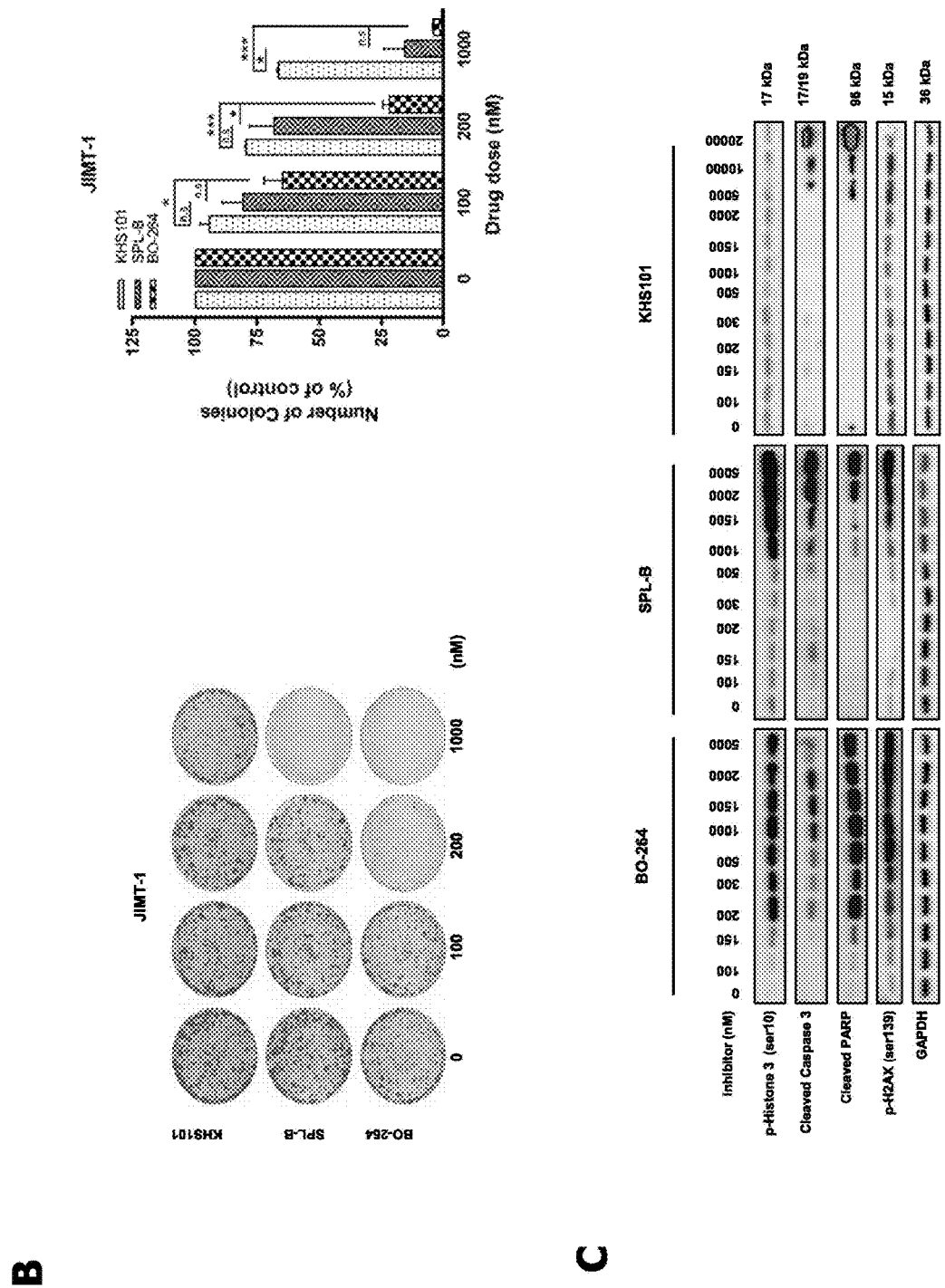

FIG. 6. BO-264 is more potent than currently available TACC3 inhibitors, SPL-B and KHS101. (A) Pharmacological inhibition of TACC3 with three different inhibitors and their effect on cell viability of breast cancer cell lines (IC50: inhibitory concentration 50%). Cell viability was measured by Cell Titer Glo kit as triplicates in all the following cell viability experiments. (B) Colony formation assay of JIMT-1 cells treated with three different TACC3 inhibitors for 12 days. Colonies were stained with crystal violet. Number of colonies was counted and analyzed using ImageJ software (lower panel). Data is presented as means±SD. (C) Western blot analysis of JIMT-1 cells treated with BO-264, SPL-B or KHS101 to test the effect of dose responses on mitotic arrest, DNA damage and apoptosis markers. The same amount of protein and the same exposure time were used in Western blot experiments to compare the effects of three drugs on these markers. *: p<0.05; : p<0.01; *: p<0.001.

Figure 7:
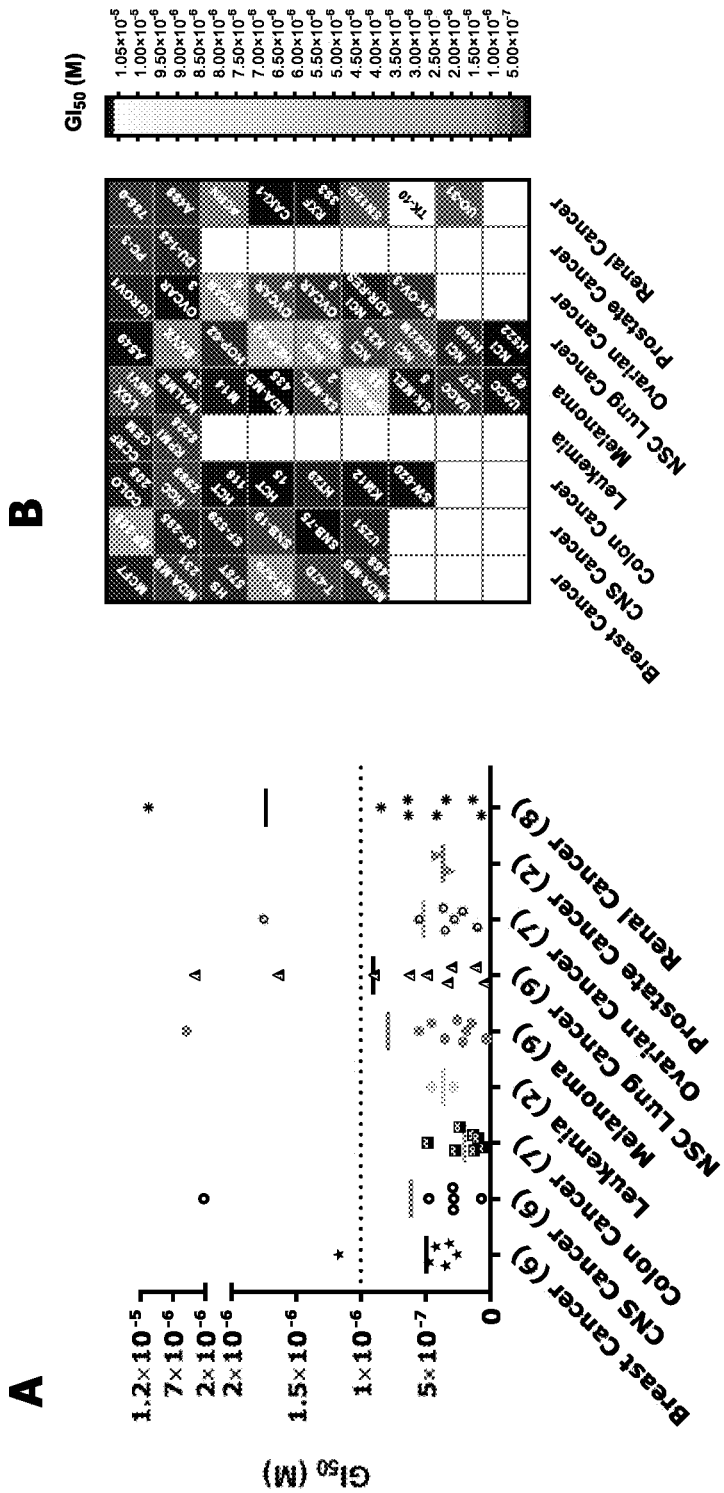

FIG. 7. NCI-60 five-dose screening reveals remarkable anti-cancer activity of BO-264 in several different tumor types. (A) Average GI50 values (M) determined from the NCI-60 five-dose screen for BO-264. Horizontal dotted line indicates 1 µM threshold. (B) Heat map data representing GI50 concentrations of BO-264 across the NCI-60 human cancer cell line panel.

Figure 8:
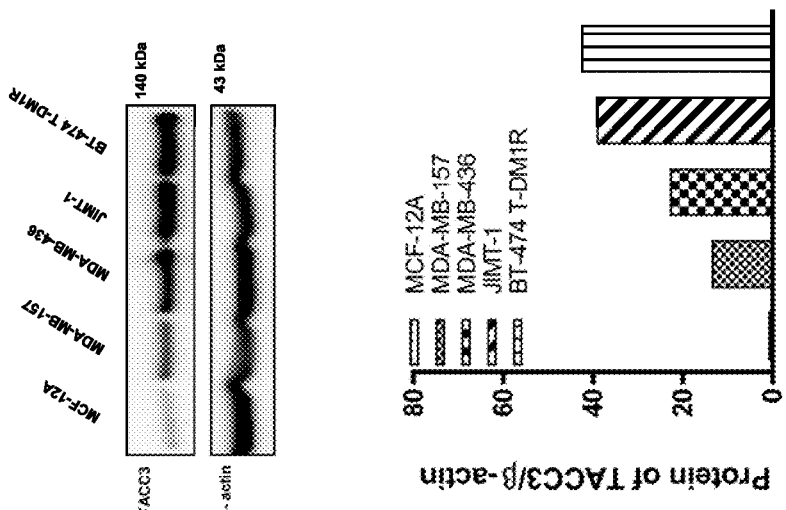
Figure 8:
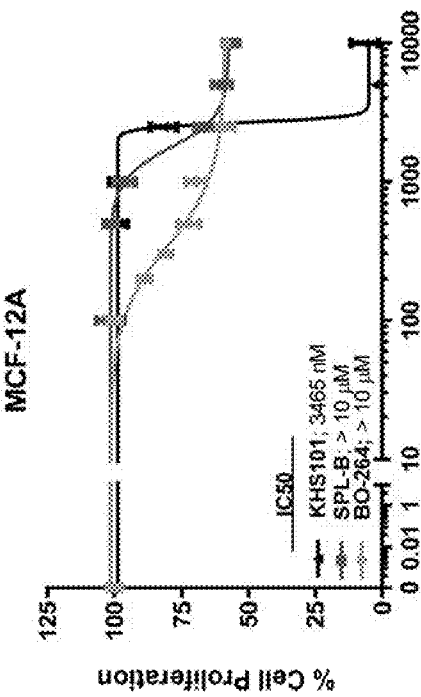

FIG. 8. BO-264 specifically and efficiently target cancer cells, but not normal cells with low level TACC3 expression. (A) Dose responses of normal breast cell line, MCF-12A, treated with increasing doses of three different TACC3 inhibitors for 72 hours. (B) TACC3 protein levels of normal breast and breast cancer cell lines. TACC3 protein levels were analyzed by Western blot. Beta actin was used as loading control. Right panel indicates TACC3 band intensities normalized to B-actin.

Figure 9:
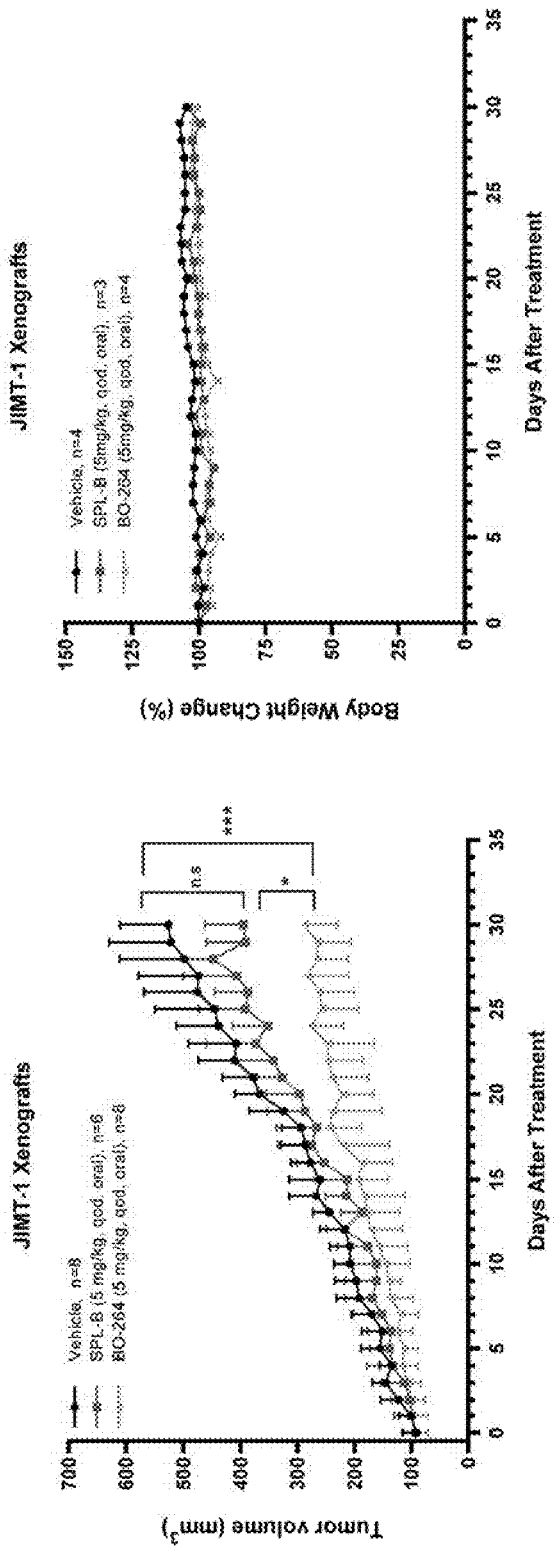

FIG. 9: BO-264 inhibits tumor growth better than SPL-B at the same low dose and administration route. (A) Tumor volume change after the application of BO-264 and SPL-B group with the same dosage and administration route. (B) Mice body weight change during the course of treatment with BO-264 and SPL-B group with the same dosage and administration route.

Figure 10:
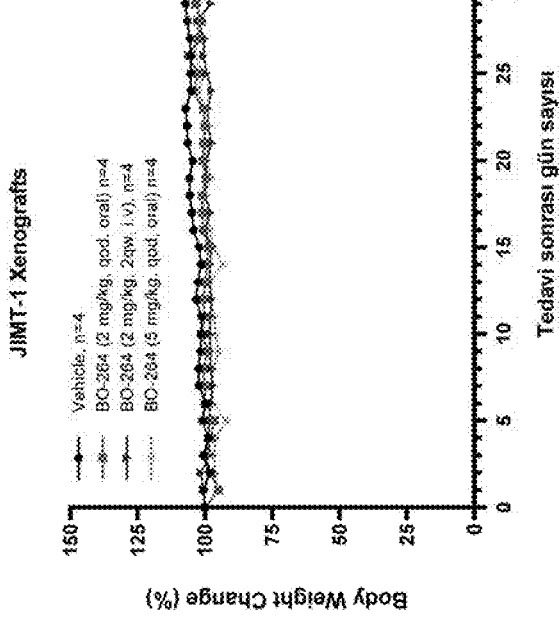
Figure 10:
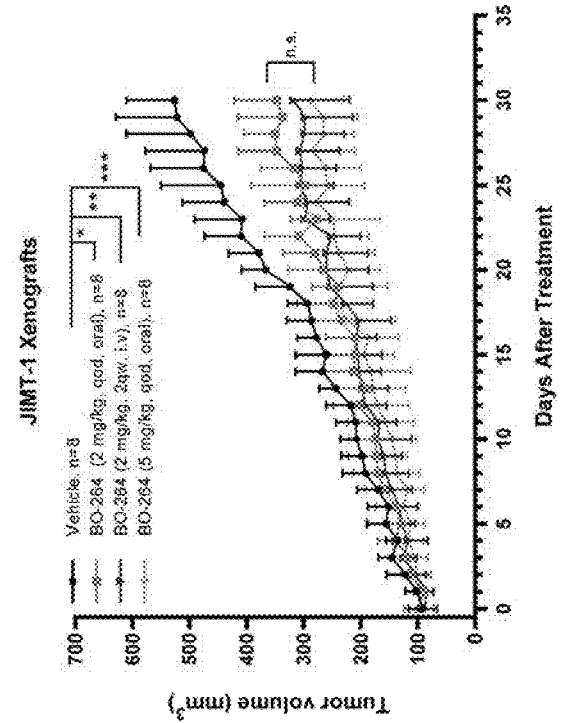

FIG. 10. Low doses and different administration routes of BO-264 inhibits tumor growth in in vivo JIMT-1 xenografts without affecting mouse body weight. (A) Tumor volume changes after the application of all three BO-264 groups with different dosage and administration routes. (B) Mice body weight change during the course of treatment with different dosages and administration ways.

Figure 11:
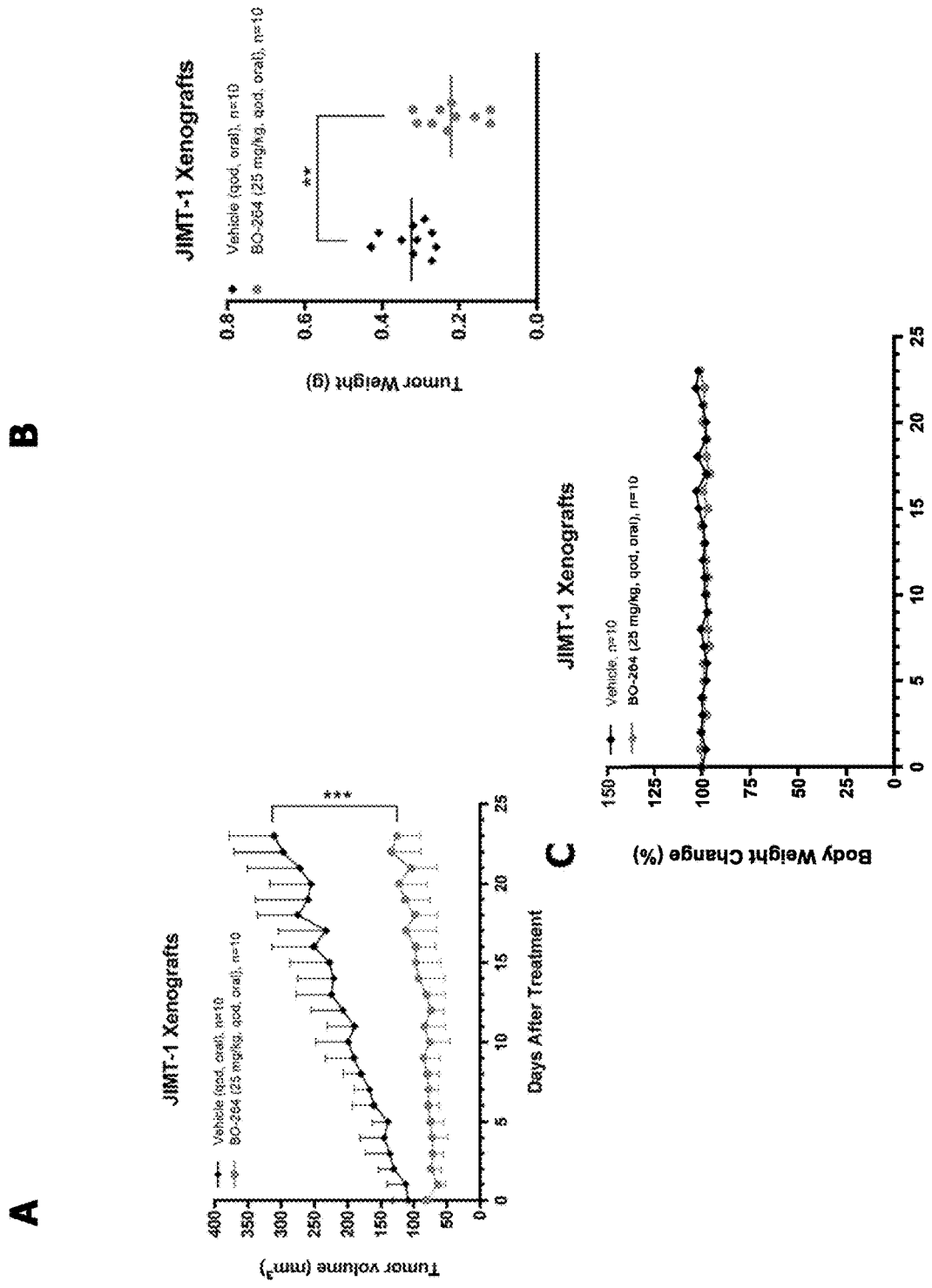

FIG. 11. BO-264 inhibits tumor growth effectively in in vivo xenografts without affecting mouse body weight. (A) Tumor volume change after the treatment with vehicle or BO-264. Treatments were started when tumors reached at around 90-100 mm$^3$. (B) Tumor weights isolated from mice treated with vehicle or BO-264. (C) Mice body weight change during the course of treatment. : $p<0.01$; *: $p<0.001$ FIG. 12. Summary of drug specific physicochemical properties. $^a$Kinetic solubility in sodium phosphate buffer at pH 7.4 at 25° C. after 2 h (Buttar et al., 2010). $^b$Log D: distribution coefficient in octanol/sodium phosphate buffer (50 mM, pH 7.4) (Unger et al., 1978). $^c$PPB: plasma protein binding assessed by equilibrium dialysis in human at 37° C. (Buttar et al., 2010). $^d$T1/2: half-life in mouse and human liver microsomes (MLM and HLM respectively) (Kalvass et al., 2001). $^e$Clint: intrinsic clearance in MLM and HLM (Kalvass et al., 2001). $^f$CYP: cytochrome P450 isozymes inhibition by BO-264 evaluated in HLM (Bourrie et al., 1996). $^g$Papp: apparent permeability coefficients in Caco-2 cell monolayer (Camenisch et al., 1998).

DESCRIPTION OF THE COMPONENTS AND PARTS OF THE INVENTION

The components shown in the figures prepared for a better explanation of the novel TACC3 inhibitor BO-264 and its synthesis and analysis is numbered separately, and explanation of each number is given below.
(1) Ethyl 4-methoxybenzoate
(2) 3-(4-Methoxyphenyl)-3-oxopropanenitrile
(3) 3-(4-Methoxyphenyl)isoxazol-5-amine
(4) N-(2-Chloropyrimidin-4-yl)-3-(4-methoxyphenyl) isoxazol-5-amine
(5) 3-(4-Methoxyphenyl)-N-(2-morpholinopyrimidin-4-yl)isoxazol-5-amine

DETAILED DESCRIPTION OF THE INVENTION

The present invention relates to a novel TACC3 inhibitor that is used five times smaller doses than other TACC3 inhibitors to reduce systemic effects in cancer therapy.

Elevated TACC3 levels are observed in many different cancer types, which makes it highly attractive target for cancer therapy. TACC3 has important roles in regulating microtubule and centrosome and maintaining spindle stability (Schneider et al., 2007; Thakur et al., 2013). To further investigate the role of TACC3 level in different tumor types, in the present invention, firstly TACC3 levels in many different cancer types and their normal tissue counterparts were analyzed (FIG. 1A). It was found that TACC3 is significantly overexpressed in many different cancer types including breast cancer. Then, different patient survival datasets using KM plotter tool were analyzed. High TACC3 levels were found to significantly correlate with worse overall survival rates in breast, lung and gastric cancer (FIG. 1B). These patient data analyses indicate that TACC3 expression level is an important factor defining the severity of the disease and patient survival. Therefore, interventions resulting in TACC3 inhibition might be a promising therapeutic strategy to improve survival of breast cancer patients.

Reduction in TACC3 levels in Hela cells has been shown to cause mitotic arrest (Schneider et al., 2007) and caspase dependent apoptosis (Kimura et al., 2013). In the present invention, it was found that breast cancer patients who expressed high TACC3 levels had an enrichment of mitotic progression and DNA repair genes supporting TACC3's oncogenic role in breast cancer development (FIG. 2A). Next, the effect of TACC3 depletion on cell viability of different breast cancer cell lines was tested. Four different breast cancer cell line models with different molecular subtypes were utilized. JIMT-1 is a HER2-positive breast cancer cell line while BT-474 T-DM1R (T-DM1 resistant) is a Luminal B subtype breast cancer cell line shown to have high TACC3 levels (Saatci et al., 2018). On the other hand, both MDA-MB-436 and MDA-MB-157 are triple negative breast cancer (TNBC) cell lines. In the present invention, firstly small interfering RNAs (siRNAs) were used to reduce the TACC3 levels in these cell lines. FIG. 2B shows that the overall TACC3 levels were reduced by approximately 60-70% after 48 h of siRNA treatment in all cell lines. Consistent with this, it was observed that TACC3 knockdown leads to significant growth inhibition of breast cancer cells (FIG. 2C). Then the possible related mechanisms that TACC3 knockdown could cause were investigated. Suppression of TACC3 levels with siRNAs in all tested breast cancer cell lines activated mitotic arrest, apoptosis and DNA damage (FIG. 2D).

As mentioned before, none of the available TACC3 inhibitors, such as KHS101 and SPL-B has yet advanced to the clinical studies. Therefore, the aim of the present invention is to develop a novel cancer therapeutic and more potent inhibitor targeting TACC3. For this purpose, it was performed in-house screening of a series of small molecules by testing their anti-proliferative effects in breast cancer cells in which TACC3 is aberrantly expressed (Ma et al., 2003; Song et al., 2018). Specifically, JIMT-1 cell line was chosen for screening the effect of compounds in cell viability due to its high TACC3 protein level compared to other tested breast cancer cell lines as well as its in vivo tumorigenicity (Saatci et al., 2018; Tanner et al., 2004) (will be discussed in FIGS. 8 and 9-10, respectively).

In the present invention, in-house screening efforts led to the identification of BO-264 as a potential TACC3 inhibitor having a significantly lower IC50 of 232 nM (FIG. 3). General procedure for the synthesis of BO-264 is indicated in FIG. 4.

To determine whether BO-264 targets TACC3, target engagement assay that is based on drug-target stabilization with increased temperature was performed in the present invention (Martinez Molina et al., 2013). For this purpose, JIMT-1 cells with vehicle, BO-264 or SPL-B (as positive control) were incubated for some time, then cell lysates were collected. A titration of TACC3 into BO-264 was carried out and monitored by recording the calorimetric and heat changes. As shown in FIG. 5, thermodynamics parameters of BO-264 binding to TACC3 at 25° C. (K: 6.23E8; ΔH: 4.929E7 cal/mol; ΔS: 1.65E5 cal/mol/deg, N: 0.704) demonstrate the interaction between these two molecules.

After that, the relative effects of TACC3 inhibitor, BO-264, with the available TACC3 inhibitors KHS101 and SPL-B on cell viability were compared. JIMT-1, MDA-MB-436, MDA-MB-157 and BT-474 T-DM1R cell lines were tested with respect to their response to these three drugs. BO-264 was found to have a significantly lower IC50 values than the two available TACC3 inhibitors in all cell lines tested (FIG. 6A). Moreover, obtaining a lower IC50 value with BO-264 in different molecular subtypes of breast cancer models indicates that our novel inhibitor has promising anti-cancer effects on breast cancer regardless of the molecular subtypes. This marked decrease in cell viability of different cancer cell lines treated with BO-264 compared to KHS101 and SPL-B was also validated with colony formation assay using JIMT-1 cells. As a result, the average colony number of JIMT-1 cells treated with BO-264 was significantly lower than the ones treated with other two inhibitors at the same doses (FIG. 6B). Therefore, the low cell viability detected with Cell Titer Glo assay and low number of colonies of JIMT-1 cells indicate that BO-264 is more effective and more potent than the other two TACC3 inhibitors, KHS101 and SPL-B in vitro. Induction of mitotic arrest, apoptosis and DNA damage processes as in case of siTACC3 treatment in breast cancer cell lines were further tested upon BO-264, SPL-B and KHS101 treatments. It was demonstrated that siTACC3-induced mitotic arrest, DNA damage and apoptosis can be recapitulated by BO-264 in a dose-dependent manner (FIG. 6C). On the other hand, similar induction levels of these markers by SPL-B and KHS101 treatment were observed at considerably higher doses as compared to BO-264 treated cells. Although higher KHS101 doses was included, which were used by others (Campo & Breuer, 2018), an induction of these markers was only observed at very high doses. Clearly, these results are consistent with the cell viability data and the IC50 values obtained through the treatment with three inhibitors (see FIG. 6A). These results further validate the 1) high potency of BO-264 with respect to nM range working doses, and 2) specificity with respect to the similar molecular alterations obtained by TACC3 downregulation using siRNAs.

These promising results in breast cancer cell lines encouraged us to test BO-264 in other cancer types. Therefore, BO-264 was screened for the anti-proliferative activity on NCI-60 human cell lines. Analysis of the five-dose screen reveals that almost all cell lines were found to be sensitive to BO-264 treatment with less than 1 µM 50% growth inhibition (GI50) value suggesting its possible applications in other cancer types (FIG. 7A). To visualize GI50 concentrations for each NCI-60 cell line, a heat map was constructed (FIG. 7B). In general, different cancer types demonstrated a very similar viability profile for BO-264.

Next, the specificity of BO-264 towards cancer cell lines over normal cells were tested. Therefore, the sensitivity of normal breast epithelial cells, MCF-12A, towards BO-264 was examined. Astonishingly, treatment even with high doses of BO-264 (5, 10 µM) did not reach to 50% growth inhibition of cells (FIG. 8A). In other words, BO-264 specifically targets tumor cells while it is ineffective in normal breast cells. As shown in FIG. 8B, MDA-MB-157, MDA-MB-436, JIMT-1 and BT-474 T-DM1R cells express high levels of TACC3 while normal breast cell line MCF-12A cells express low TACC3 level. This shows that sensitivity to BO-264 correlates with aberrant TACC3 expression level in cancer cells. Besides, the low TACC3 levels might explain why MCF-12A cells did not respond to any of the TACC3 inhibitors at low doses.

The results described above demonstrated that breast cancer cells expressing high TACC3 levels are more sensitive to present novel invention TACC3 inhibitor, BO-264, in vitro. Therefore, the effect of BO-264 compared to SPL-B on tumor growth of highly tumorigenic cell line JIMT-1 (Barok et al., 2007; Tanner et al., 2004) in immunodeficient mice was tested. For this purpose, female nude mice were injected with JIMT-1 cells into mammary fat pad (MFP) and subsequently treated with vehicle or 5 mg/kg (oral) BO-264 or SPL-B was applied every two days for 30 days. It was concluded that BO-264 showed significant reduction of tumor growth as compared to SPL-B, and there were no negative effects on the body weight of mice (FIG. 9).

Then, different doses and administration routes of low dose BO-264 were tested using JIMT-1 xenografts. BO-264 2 mg/kg (oral or i.v) or 5 mg/kg (oral) every two days for 30 days was administered into mice (FIG. 10). Tumor growth rate of all three BO-264-administrated group decreased when compared with control group and among these group, 5 mg/kg (oral) showed the most significant effect on tumor growth (FIG. 10A). It is indicated in FIG. 10B that application of BO-264 did not have any negative effect on the body weight of mice.

Moreover; to test the effect of a higher BO-264 dose tumor growth compared to previous experiments to obtain better anti-tumor effect and test its tolerability, female nude mice were injected with JIMT-1 cells into mammary fat pad (MFP) and subsequently treated with vehicle or BO-264 (25 mg/kg oral) for 23 days (FIG. 11). BO-264 showed very significant reduction of tumor growth compared to vehicle-treated mice (FIG. 11A). Tumor weights were significantly lower when compared to the ones of vehicle group (FIG. 11B). Importantly, BO-264 was well tolerated since treatment did not affect the mice weight (FIG. 11C).

On the basis of the overall profile, BO-264 was evaluated for its physiochemical properties and metabolic stability. BO-264 has a medium lipophilicity with a log $D_{7.4}$ of 2.3 and showed low solubility as well as low stability in both human and mouse liver microsomes, and relatively high plasma protein binding (unbound fraction of 1.13%), but good Caco-2 permeability with a low efflux ratio (AB=190× $10^{-6}$ nm/s, ratio=<2.0) (FIG. 12). Concordantly, cytochrome P450 inhibition by BO-264 in human liver microsomes was also characterized in order to evaluate potential drug-drug interactions (Lin & Lu, 1998) (FIG. 12). Accordingly, BO-264 was a moderate inhibitor of CYP2C9 (IC50=2.63 µM) and CYP3A (testosterone as substrate; IC50=8.59 µM) whereas it was a weak or not an inhibitor of CYP2CD6 (IC50=18.46 µM) and CYP3A (IC50=midazolam as substrate; 30.04 µM), indicating that BO-264 has low activity on the tested P450 cytochromes.

Materials and Methods

Cell Culture and Reagents

MDA-MB-436, MDA-MB-157 and MCF-12A cell lines were obtained from ATCC. T-DM1 resistant HER2-positive breast cancer cell line BT-474 T-DM1R was developed and characterized as described previously (Saatci et al., 2018). Cells were cultured in Dulbecco's modified Eagle's medium (Lonza, NJ, USA), supplemented with 10% fetal bovine serum (Lonza), 1% non-essential amino acid and 50 U/ml penicillin/streptomycin. BT-474 T-DM1R cells were also supplemented with 0.1% insulin (Sigma Aldrich, MO, USA). In addition, MCF-12A cells were grown in 20 ng/ml epidermal growth factor (EGF) and 500 ng/ml hydrocortisone containing medium. All cell lines were tested regularly using MycoAlert *Mycoplasma* Detection Kit (Lonza).

Synthesis and Analysis of BO-264

For the synthesis of BO-264, synthetic procedure outlined in FIG. 3 was utilized. Starting from 4-methoxybenzoic acid, ethyl 4-methoxybenzoate (1) was generated through the esterification of the carboxylic acid group. Following the described conditions in Scheme 1,3-(4-methoxyphenyl)-3-oxopropanenitrile (2) was obtained. 3-(4-methoxyphenyl)-3-oxopropanenitrile (2) intermediate was then treated with hydroxylamine to obtain 3-(4-methoxyphenyl) isoxazol-5- amine (3). 5-Aminoisoxazol intermediate (3) underwent a nucleophilic aromatic substitution reaction with 2,4-dichloropyrimidine to afford N-(2-chloropyrimidin-4-yl)-3-(4-methoxyphenyl) isoxazol-5-amine (4). Lastly, compound 4 was treated with morpholine to obtain the final compound 3-(4-methoxyphenyl)-N-(2-morpholinopyrimidin-4-yl) isoxazol-5-amine (5, BO-264).

Ethyl 4-methoxybenzoate (1)

Thionyl chloride ($SOCl_2$) (34.4 mmol, 2.27 equiv) was added dropwise to a solution of 4-methoxybenzoic acid (15.15 mmol, 1 equiv) in absolute ethanol (25 ml) at RT. The reaction was stirred at 80° C. for 3 h. After the reaction was complete, the resulting mixture was concentrated under reduced pressure to give colorless liquid (86% yield). HRMS (m/z): $[M+H]^+$ calculated for $C_{10}H_{13}O_3$: 181.0865; found: 181.0858.

3-(4-Methoxyphenyl)-3-oxopropanenitrile (2)

Sodium hydride (NaH) (60% dispersion in mineral oil) (27.501 mmol, 3 equiv) and acetonitrile (MeCN) (27.501 mmol, 3 equiv) were added to a solution of ethyl 4-methoxybenzoate (1) (9.167 mmol, 1 equiv) in dry toluene at RT, and then refluxed under nitrogen atmosphere for 2 h. The resulting mixture was cooled to RT. The salt obtained was washed with petroleum ether and then filtered in vacuo. The salt was dissolved in water and then acidified with concentrated hydrochloric acid (HCl). The resulting solid was filtered and triturated with a solution of sodium bicarbonate ($NaHCO_3$), and then filtered to give light yellow solid. Yield: 77%. MP: 127.5-129.4° C. HRMS (m/z): $[M-H]-$ calculated for $C_{10}H_8NO_2$: 174.0561; found: 174.0564

3-(4-Methoxyphenyl)isoxazol-5-amine (3)

3-(4-methoxyphenyl)-3-oxopropanenitrile (2) (2.8571 mmol, 1 equiv) and hydroxylamine hydrochloride ($H_2NOH.HCl$) (2.8856 mmol, 1.05 equiv) were added to solution of sodium hydroxide (NaOH) (5.8570 mmol, 2.05 equiv) in water. The reaction mixture was refluxed for 4 h. After the resulting mixture cooled down to RT, it was diluted with water and extracted with dichloromethane (DCM). The organic layer was dried, filtered and evaporated to give the crude product, which was purified by automated-flash chromatography on silica gel (24 g) eluting with a gradient of 0-60% ethyl acetate (EtOAc) in hexane. Yield 59%. MP: 135.4-137.2° C. HRMS (m/z): $[M+H]+$ calculated for $C_{10}H_{11}N_2O_2$: 191.0821; found: 191.0812

N-(2-Chloropyrimidin-4-yl)-3-(4-methoxyphenyl) isoxazol-5-amine (4)

Potassium tert-butoxide (t-BuOK) (2.4025 mmol, 2.5 equiv) was added to a 3-(4-methoxyphenyl)isoxazol-5-amine (3) solution (0.961 mmol, 1 equiv) in tert-butanol and the mixture was stirred for 1 h at RT. 2,4-Dichloropyrimidine (1.441 mmol, 1.5 equiv) was added to the reaction mixture, and it was stirred for 24 h at RT. After the reaction was complete, the mixture was quenched by aqueous ammonium chloride ($NH_4Cl$) solution and then extracted with EtOAc. The organic layer was dried, filtered and evaporated to give the crude product, which was purified by automated-flash chromatography on silica gel (24 g), eluting with a gradient of 0-60% EtOAc in DCM. Yield: 42%. MP: 197-198.8° C. (dec). HRMS (m/z): $[M+H]+$ calculated for $C_{14}H_{12}N_4O_2Cl$: 303.0649; found: 303.0645. $^1$H NMR (400 MHz, DMSO): δ 3.82 (3H, s), 6.68 (1H, s), 7.01 (1H, d, J=5.8 Hz), 7.07 (2H, d, J=8.6 Hz), 7.77 (2H, d, J=8.6 Hz), 8.40 (1H, d, J=5.8 Hz), 11.73 (1H, s). $^{13}$C NMR (100 MHz, DMSO): δ 55.22, 85.54, 106.48, 114.42, 121.06, 127.86, 158.60, 158.72, 159.40, 160.69, 161.51, 162.26.

3-(4-Methoxyphenyl)-N-(2-morpholinopyrimidin-4-yl)isoxazol-5-anine (5) (BO-264)

Morpholine (1.0746 mmol, 3 equiv) was added to a solution of N-(2-chloropyrimidin-4-yl)-3-(4-methoxyphenyl)isoxazol-5-amine (4) (0.3582 mmol, 1 equiv) in n-butanol. The reaction mixture was refluxed under nitrogen atmosphere for 5 h. After the reaction was complete, the mixture cooled down to RT, and then quenched by ice water to give light yellow solid. The resulting solid filtered, dried to give crude product which was purified by automated-flash chromatography on silica gel (24 g), eluting with a gradient of 0-60% EtOAc in DCM. Yield: 70%. MP: 192.5-194.2° C. HRMS (m/z): $[M+H]+$ calculated for $C_{18}H_{20}N_5O_3$: 354.1566; found: 354.1572. $^1$H NMR (400 MHz, DMSO): δ 3.68-3.70 (8H, m), 3.80 (3H, s), 6.24 (1H, d, J=5.6 Hz), 6.54 (1H, s), 7.04 (2H, d, J=9.0 Hz), 7.74 (2H, d, J=9.0 Hz), 8.11 (1H, d, J=5.6 Hz), 10.98 (1H, s). $^{13}$C NMR (100 MHz, DMSO): δ 44.10, 55.24, 65.99, 84.03, 97.00, 114.43, 121.43, 127.87, 157.38, 157.45, 160.61, 161.37, 162.13, 162.61.

Isothermal Titration Calorimetry (ITC)

Purified TACC3 recombinant protein (TP310754; Origene, MD, USA) and BO-264 (5) were prepared in 25 mM Tris.HCl, pH 7.3, 100 mM glycine, 10% glycerol solution. BO-264 (5) was loaded into the sample cell and titrated with TACC3 protein (10-fold higher concentration in the syringe) in duplicate experiments. Titrations were carried out using Microcal 200 equipment (GE Healthcare, Austria) at 25° C. For each titration, 10 injections were made with 6 min spacing. The reference power was set at 2 μcal/sec, and the sample cell was continuously stirred at 500 rpm. In order to assess the binding efficiency between drug and protein, background data obtained by protein injected into buffer alone was subtracted from the experimental isotherms. The data was analyzed using Origin 7 Software provided along with the ITC200, and binding parameters such as association constant (Ka), number of binding sites (N) and enthalpy (ΔH) were calculated.

Inhibitor Treatments and Cell Viability Assay

KHS101 and SPL-B were dissolved in 100% DMSO to yield a stock concentration of 50 mM. Newly synthesized molecules were dissolved in 100% DMSO to yield a stock concentration of 10 mM. For cell viability assay, JIMT-1 ($3×10^3$ cells/well), BT-474 T-DM1R ($6×10^3$ cells/well), MDA-MB-436 ($4×10^3$ cells/well), MDA-MB-157 ($3×10^3$ cells/well) and MCF-12A ($5×10^3$ cells/well) cells were seeded, and 24 hours after cell seeding inhibitor treatments were performed at different concentrations. Cell viability was measured 72 hours after treatment with Cell Titer Glo assay as recommended by the manufacturer. For western blotting, different concentrations of KHS101, SPL-B or BO-264 were given to JIMT-1 cells ($1.5×10^5$ cells/well) for 24 hours.

Transient Transfection with siRNAs

For cell viability assays, JIMT-1 ($3×10^3$ cells/well), BT-474 T-DM1R ($6×10^3$ cells/well), MDA-MB-436 ($4×10^3$ cells/well) and MDA-MB-157 ($3×10^3$ cells/well), cells were seeded into 96-well plates in P/S-free growth medium. 24 hours after seeding, cells were transfected with two different siRNAs targeting TACC3 (Dharmacon, CO, USA) at a final concentration of 20 nM (siTACC3 #1: D-004155-03 and siTACC3 #2: D-004155-02) using Lipofectamine 2000™ (Invitrogen, CA) transfection reagent as described previously (Mutlu et al., 2016). 72 hours following transfection, cell viability was measured using Cell Titer Glo assay. To assess the TACC3 knockdown levels upon siRNA transfections, JIMT-1 ($1.5 \times 10^5$ cells/well), BT-474 T-DM1R ($2 \times 10^5$ cells/well), MDA-MB-436 ($1.5 \times 10^5$ cells/well) and MDA-MB-157 ($1.5 \times 10^5$ cells/well) cells were transfected with two different TACC3 siRNAs for 48 hours. Knockdown efficiency at mRNA and protein levels was analyzed by quantitative real-time PCR (qRT-PCR) and western blotting, respectively.

Colony Formation Assay

For monolayer culture, single-cell suspensions of JIMT-1 cells ($3 \times 10^3$ cells/well) were plated in a 12-well plate. After 6 hours incubation, cells were treated with different doses of BO-264 (5), SPL-B and KHS101. For both experimental setups, the media were refreshed every 4 days, and cells were incubated for 12 days. Cells were then fixed with 2% paraformaldehyde for 15 min and stained with 1% crystal violet (Merck, Darmstadt, Germany) for 15 min at RT. Surviving colonies (composed of at least 50 cells) were counted with ImageJ software (NIH).

NCI-60 Cancer Cell Line Panel Screening

BO-264 (5) was submitted to the National Cancer Institute (NCI number 5807620) for NCI-60 human cell line screening which consists of 60 human cancer cell lines from different cancer types. BO-264 (5) was first accepted for single-dose screens at a concentration of 10 µM, which determines the percentage growth inhibition of each cell line. Then, it was selected for five-dose NCI-60 screen at doses ranging from 10 nM to 100 µM, which determines the GI50 (50% growth inhibition), TGI (total growth inhibition) and LC50 (lethal dose concentration inducing 50% cell death) values for 60 cell lines. Detailed screening methodology can be accessed from the National Cancer Institute webpage. Briefly, 24 h after cell seeding into 96-well plates, they were treated with 5-log M concentration range of the compound for 2 days. Cytotoxicity was assessed using sulphorhodamine B (SRB) assay.

Breast Cancer Xenograft Experiments

Six-to-eight-week-old female athymic nude mice were housed with a temperature-controlled and 12-hour light/12-hour dark cycle environment. This study was carried out in accordance with Institutional Animal Care and Use Committee of Bilkent University and performed according to the institution's guidelines and animal research principles. For in vivo tumor growth, $4 \times 10^6$ JIMT-1 cells were prepared in 150 µl of 1:1 DMEM and Matrigel (Corning, N.Y., USA), v/v) and injected into the mammary fat pads (MFP) of female nude mice. Mouse weight and tumor volume were measure daily using calipers. Tumor volumes were calculated as length×width×0.5. Once the tumor volume had reached about 100 mm³, xenografts were randomized into groups. Animals were treated with vehicle (0.75% HPMC (hydroxypropyl methylcellulose) in ddH2O and 10% Tween-80), or BO-264 (every other day at different doses and administration ways). The effect of BO-264 on tumor growth was also compared with SPL-B. Mice were sacrificed 20-30 days after initiation of the treatment, and the tumors were collected and stored for subsequent analyses.

Bioinformatics Analysis

TACC3 expression in different tumor and normal tissues was analyzed using The Cancer Genome Atlas (TCGA) data (Akbani et al., 2014). The association between TACC3 expression and patient overall survival was analyzed using Kaplan Meier plotter database, which includes information on overall survival of 1402 breast cancer (Gyorffy et al., 2010), 1926 lung cancer (Gyorffy, Surowiak, Budczies, & Lanczky, 2013) and 876 gastric cancer (Szasz et al., 2016) patients. Gene set enrichment analysis (GSEA) analysis of mitosis and DNA repair-related gene sets, available at the Broad Institute website, was done using breast cancer METABRIC Validation data set (n=995) where patients were divided into two groups (high vs. low) based on TACC3 expression levels.

Statistical Analysis

Data were analyzed using GraphPad Prism software (GraphPad Software, Inc) and expressed as mean±standard deviation from three independent experiments. Statistical significance was determined by two-tailed Student's t-test. A p and an adjusted p (q) value of less than 0.05 were considered to be statistically significant.

REFERENCES

Akbani, R., Ng, P. K., Werner, H. M., Shahmoradgoli, M., Zhang, F., Ju, Z., . . . Mills, G. B. (2014). A pan-cancer proteomic perspective on The Cancer Genome Atlas. Nat Commun, 5, 3887. doi:10.1038/ncomms4887

Barok, M., Isola, J., Palyi-Krekk, Z., Nagy, P., Juhasz, I., Vereb, G., . . . Szollosi, J. (2007). Trastuzumab causes antibody-dependent cellular cytotoxicity-mediated growth inhibition of submacroscopic JIMT-1 breast cancer xenografts despite intrinsic drug resistance. Mol Cancer Ther, 6(7), 2065-2072. doi:10.1158/1535-7163.MCT-06-0766

Campo, L., & Breuer, E. K. (2018). Inhibition of TACC3 by a small molecule inhibitor in breast cancer. Biochem Biophys Res Commun, 498(4), 1085-1092. doi:10.1016/j.bbrc.2018.03.125

Chan, K. S., Koh, C. G., & Li, H. Y. (2012). Mitosis-targeted anti-cancer therapies: where they stand. Cell Death Dis, 3, e411. doi:10.1038/cddis.2012.148

Curtis, C., Shah, S. P., Chin, S. F., Turashvili, G., Rueda, O. M., Dunning, M. J., . . . Aparicio, S. (2012). The genomic and transcriptomic architecture of 2,000 breast tumours reveals novel subgroups. Nature, 486(7403), 346-352. doi: 10.1038/nature10983

Dominguez-Brauer, C., Thu, K. L., Mason, J. M., Blaser, H., Bray, M. R., & Mak, T. W. (2015). Targeting Mitosis in Cancer: Emerging Strategies. Mol Cell, 60(4), 524-536. doi:10.1016/j.molcel.2015.11.006

Gascoigne, K. E., & Taylor, S. S. (2009). How do anti-mitotic drugs kill cancer cells? J Cell Sci, 122 (Pt 15), 2579-2585. doi:10.1242/jcs.039719

Guo, F., & Liu, Y. (2018). Knockdown of TACC3 Inhibits the Proliferation and Invasion of Human Renal Cell Carcinoma Cells. Oncol Res, 26(2), 183-189. doi: 10.3727/096504017X14837020772250

Gyorffy, B., Lanczky, A., Eklund, A. C., Denkert, C., Budczies, J., Li, Q., & Szallasi, Z. (2010). An online survival analysis tool to rapidly assess the effect of 22,277 genes on breast cancer prognosis using microarray data of 1,809 patients. Breast Cancer Res Treat, 123(3), 725-731. doi:10.1007/s10549-009-0674-9

Gyorffy, B., Surowiak, P., Budczies, J., & Lanczky, A. (2013). Online survival analysis software to assess the prognostic value of biomarkers using transcriptomic data in non-small-cell lung cancer. PLoS One, 8(12), e82241. doi:10.1371/journal.pone.0082241

Kimura, M., Yoshioka, T., Saio, M., Banno, Y., Nagaoka, H., & Okano, Y. (2013). Mitotic catastrophe and cell death induced by depletion of centrosomal proteins. Cell Death Dis, 4, e603. doi:10.1038/cddis.2013.108

Lin, J. H., & Lu, A. Y. (1998). Inhibition and induction of cytochrome P450 and the clinical implications. Clin Pharmacokinet, 35(5), 361-390. doi:10.2165/00003088-199835050-00003

Ma, X. J., Salunga, R., Tuggle, J. T., Gaudet, J., Enright, E., McQuary, P., . . . Sgroi, D. C. (2003). Gene expression profiles of human breast cancer progression. Proc Natl Acad Sci USA, 100(10), 5974-5979. doi:10.1073/pnas.0931261100

Martinez Molina, D., Jafari, R., Ignatushchenko, M., Seki, T., Larsson, E. A., Dan, C., . . . Nordlund, P. (2013). Monitoring drug target engagement in cells and tissues using the cellular thermal shift assay. Science, 341(6141), 84-87. doi:10.1126/science.1233606

Marzo, I., & Naval, J. (2013). Antimitotic drugs in cancer chemotherapy: promises and pitfalls. Biochem Pharmacol, 86(6), 703-710. doi:10.1016/j.bcp.2013.07.010

Mutlu, M., Saatci, O., Ansari, S. A., Yurdusev, E., Shehwana, H., Konu, O., . . . Sahin, O. (2016). miR-564 acts as a dual inhibitor of PI3K and MAPK signaling networks and inhibits proliferation and invasion in breast cancer. Sci Rep, 6, 32541. doi:10.1038/srep32541

Polson, E. S., Kuchler, V. B., Abbosh, C., Ross, E. M., Mathew, R. K., Beard, H. A., . . . Wurdak, H. (2018). KHS101 disrupts energy metabolism in human glioblastoma cells and reduces tumor growth in mice. Sci Transl Med, 10(454). doi:10.1126/scitranslmed.aar2718

Saatci, O., Borgoni, S., Akbulut, O., Durmus, S., Raza, U., Eyupoglu, E., . . . Sahin, O. (2018). Targeting PLK1 overcomes T-DM1 resistance via CDK1-dependent phosphorylation and inactivation of Bcl-2/xL in HER2-positive breast cancer. Oncogene, 37(17), 2251-2269. doi:10.1038/s41388-017-0108-9

Sanchez-Martinez, C., Gelbert, L. M., Lallena, M. J., & de Dios, A. (2015). Cyclin dependent kinase (CDK) inhibitors as anticancer drugs. Bioorg Med Chem Lett, 25(17), 3420-3435. doi:10.1016/j.bmcl.2015.05.100

Schmidt, S., Schneider, L., Essmann, F., Cirstea, I. C., Kuck, F., Kletke, A., . . . Piekorz, R. P. (2010). The centrosomal protein TACC3 controls paclitaxel sensitivity by modulating a premature senescence program. Oncogene, 29(46), 6184-6192. doi:10.1038/onc.2010.354

Schneider, L., Essmann, F., Kletke, A., Rio, P., Hanenberg, H., Wetzel, W., . . . Piekorz, R. P. (2007). The transforming acidic coiled coil 3 protein is essential for spindle-dependent chromosome alignment and mitotic survival. J Biol Chem, 282(40), 29273-29283. doi:10.1074/jbc.M704151200

Singh, P., Thomas, G. E., Gireesh, K. K., & Manna, T. K. (2014). TACC3 protein regulates microtubule nucleation by affecting gamma-tubulin ring complexes. J Biol Chem, 289(46), 31719-31735. doi:10.1074/jbc.M114.575100

Song, H., Liu, C., Shen, N., Yi, P., Dong, F., Li, X., . . . Huang, T. (2018). Overexpression of TACC3 in Breast Cancer Associates With Poor Prognosis. Appl Immunohistochem Mol Morphol, 26(2), 113-119. doi:10.1097/PAI.0000000000000392

Strebhardt, K., & Ullrich, A. (2006). Targeting polo-like kinase 1 for cancer therapy. Nat Rev Cancer, 6(4), 321-330. doi:10.1038/nrc1841

Szasz, A. M., Lanczky, A., Nagy, A., Forster, S., Hark, K., Green, J. E., . . . Gyorffy, B. (2016). Cross-validation of survival associated biomarkers in gastric cancer using transcriptomic data of 1,065 patients. Oncotarget, 7(31), 49322-49333. doi:10.18632/oncotarget.10337

Tang, A., Gao, K., Chu, L., Zhang, R., Yang, J., & Zheng, J. (2017). Aurora kinases: novel therapy targets in cancers. Oncotarget, 8(14), 23937-23954. doi:10.18632/oncotarget.14893

Tanner, M., Kapanen, A. I., Junttila, T., Raheem, O., Grenman, S., Elo, J., . . . Isola, J. (2004). Characterization of a novel cell line established from a patient with Herceptin-resistant breast cancer. Mol Cancer Ther, 3(12), 1585-1592.

Thakur, H. C., Singh, M., Nagel-Steger, L., Prumbaum, D., Fansa, E. K., Gremer, L., . . . Piekorz, R. P. (2013). Role of centrosomal adaptor proteins of the TACC family in the regulation of microtubule dynamics during mitotic cell division. Biol Chem, 394(11), 1411-1423. doi:10.1515/hsz-2013-0184

Wurdak, H., Zhu, S., Min, K. H., Aimone, L., Lairson, L. L., Watson, J., . . . Schultz, P. G. (2010). A small molecule accelerates neuronal differentiation in the adult rat. Proc Natl Acad Sci USA, 107(38), 16542-16547. doi:10.1073/pnas.1010300107

Yao, R., Kondoh, Y., Natsume, Y., Yamanaka, H., Inoue, M., Toki, H., . . . Noda, T. (2014). A small compound targeting TACC3 revealed its different spatiotemporal contributions for spindle assembly in cancer cells. Oncogene, 33(33), 4242-4252. doi:10.1038/onc.2013.382

Yao, R., Natsume, Y., Saiki, Y., Shioya, H., Takeuchi, K., Yamori, T., . . . Noda, T. (2012). Disruption of Tacc3 function leads to in vivo tumor regression. Oncogene, 31(2), 135-148. doi: 10.1038/onc.2011.235

The invention claimed is:

1. A compound represented by Formula I or a pharmaceutically acceptable salt thereof:

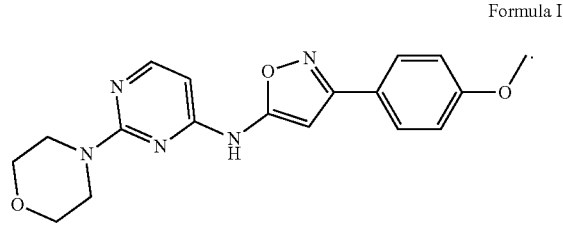 [SMILES: COc1ccc(-c2cc(Nc3ccnc(N4CCOCC4)n3)on2)cc1]

Formula I

2. The compound of claim 1, wherein the compound is not a salt.

3. The compound of claim 1, wherein the compound is a pharmaceutically acceptable salt of the compound represented by Formula I.

4. A method of treating cancer, comprising administering the compound of claim 1 to a subject in need thereof, wherein the cancer is breast cancer, colon cancer, melanoma, lung cancer, central nervous system cancer, ovarian cancer, leukemia, renal cancer or prostate cancer.

5. The method of claim 4, wherein the compound is not a salt.

6. The method of claim 5, wherein the cancer is breast cancer, colon cancer, or ovarian cancer.

7. The compound of claim 4, wherein the compound is a pharmaceutically acceptable salt of the compound represented by Formula I.

8. The method of claim 7, wherein the cancer is breast cancer, colon cancer, or ovarian cancer.

9. A method of inducing mitotic arrest, apoptosis or DNA damage in a cell, comprising contacting the cell with a compound of claim 1.

10. The method of claim 9, wherein the compound is not a salt.

11. The method of claim 10, wherein the method induces mitotic arrest in a cell.

12. The method of claim 10, wherein the method induces apoptosis in a cell.

13. The method of claim 10, wherein the method induces DNA damage in a cell.

14. The compound of claim 9, wherein the compound is a pharmaceutically acceptable salt of the compound represented by Formula I.

15. The method of claim 14, wherein the method induces mitotic arrest in a cell.

16. The method of claim 14, wherein the method induces apoptosis in a cell.

17. The method of claim 14, wherein the method induces DNA damage in a cell.

18. A pharmaceutical composition comprising the compound of claim 1 and pharmaceutically acceptable excipient.

\* \* \* \* \*